(12) United States Patent
Johnson et al.

(10) Patent No.: US 8,404,644 B2
(45) Date of Patent: Mar. 26, 2013

(54) AGENTS WITH ANGIOGENIC AND WOUND HEALING ACTIVITY

(75) Inventors: Keryn Johnson, Wellington (NZ); Madhusudan Vasudevamurthy, Christchurch (NZ)

(73) Assignees: Meat & Livestock Australia Limited, North Sydney (AU); Industrial Research Limited, Lower Hutt (NZ)

( * ) Notice: Subject to any disclaimer, the term of this patent is extended or adjusted under 35 U.S.C. 154(b) by 254 days.

(21) Appl. No.: 12/676,295

(22) PCT Filed: Sep. 5, 2008

(86) PCT No.: PCT/AU2008/001319
§ 371 (c)(1),
(2), (4) Date: Apr. 27, 2010

(87) PCT Pub. No.: WO2009/029991
PCT Pub. Date: Mar. 12, 2009

(65) Prior Publication Data
US 2010/0210531 A1 Aug. 19, 2010

(30) Foreign Application Priority Data

Sep. 7, 2007 (AU) ................................ 2007904857

(51) Int. Cl.
*A61K 38/17* (2006.01)
*C07K 1/14* (2006.01)
(52) U.S. Cl. .................. 514/21.2; 530/350; 530/422
(58) Field of Classification Search ............ 514/12, 514/21.2; 530/422, 350
See application file for complete search history.

(56) References Cited

U.S. PATENT DOCUMENTS

| | | | |
|---|---|---|---|
| 2006/0211057 A1 | 9/2006 | Azar et al. | |
| 2008/0138353 A1 | 6/2008 | Steinman et al. | |
| 2009/0142295 A1 | 6/2009 | Becker | |
| 2009/0220450 A1 | 9/2009 | Green et al. | |
| 2010/0210531 A1* | 8/2010 | Johnson et al. | 514/12 |

FOREIGN PATENT DOCUMENTS

| | | |
|---|---|---|
| WO | WO-99/51634 A1 | 10/1999 |
| WO | WO-99/51738 A1 | 10/1999 |
| WO | WO-03096981 A2 | 11/2003 |
| WO | 2004/005883 A2 | 1/2004 |
| WO | 2004/096277 A1 | 11/2004 |
| WO | 2005/004894 A2 | 1/2005 |
| WO | WO-2006091930 A2 | 8/2006 |
| WO | WO-2006134494 A2 | 12/2006 |
| WO | WO-2007084895 A2 | 7/2007 |
| WO | 2008/005021 A1 | 1/2008 |
| WO | WO-2008060622 A2 | 5/2008 |
| WO | WO-2008073466 A2 | 6/2008 |
| WO | WO-2009012224 A2 | 1/2009 |

OTHER PUBLICATIONS

Mok et al., Biochem. J. 104, 128-134 (1967).*
Sathish et al., J. Biol. Chem. 279, 16425-16432 (2004).*
EPO Form 1224, Nov. 11, 2010, Suppl. European Search Rpt. for PCT/AU2008/001319.
Head, M.W., Peter, A., Clayton, R.M. (1991). Evidence for the extralenticular expression of members of the β-crystallin gene family in the chick and a comparison with δ-crystallin during differentiation and transdifferentiation. Differentiation. 48 (3), pp. 147-156.
Hejtmancik, J. Fielding et al. Association properties of βB2- and βA3-crystallin: ability to form dimers. Protein Engineering. vol. 10, No. 11, pp. 1347-1352, 1997.
Hejtmancik, J. F. et al. β-crystallin association. Experimental Eye Research. 79, 2004, pp. 377-383.
Herbrink, Paul and Bloemendal, Hans. I. Studies on β crystallin. Isolation and partial characterization of the principal polypeptide chain. 1974. Biochimica et Biophysica Acta. 336, pp. 370-382.
Hoehenwarter, W., Klose, J. and Jungblut, P.R. Eye lens proteomics. Amino Acids. 2006. 30, pp. 369-389.
Jaenicke, R. And Slingsby, C. Lens Crystallins and Their Microbial Homologs: Structure, Stability, and Function. Critical Reviews in Biochemistry and Molecular Biology, 36(5):435-499 (2001).
Jobby, M.K. and Sharma, Y. Rapid purification of recombinant βB2-crystallin using hydrophobic interaction chromatography. Protein Expression and Purification. 28, 2003, pp. 158-164.
Jobby, M.K. and Sharma, Y. Calcium-binding to lens βB2- and βA3-crystallins suggests that all β-crystallins are calcium-binding proteins. FEBS Journal. 2007, 274, pp. 4135-4147.
Kantorow, M. and Horwitz, J. Extralenticular expression, cAMP-dependent kinase phosphorylation and autophosphorylation of βB2-crystallin. Investigative Ophthalmology and Visual Science, vol. 38, Issue 4, 1997. S205—Conference Abstract.
Kantorow, M. and Piatigorsky, J. Phosphorylations of αA- and αB-crystallin. International Journal of Biological Macromolecules. 22, 1998, pp. 307-314.
Kasaj, A., Willershausen, B., Berakdar, M., Tekyatan, H. and Sculean, A., (2006). Effect of oily calcium hydroxide suspension on early wound healing after non-surgical periodontal therapy. Clinical Oral Investigations. 10, pp. 72-76.
Kilby, G. W., et al. Loss of the C-terminal serine residue from bovine βB2-crystallin. Exp. Eye. Res. 1995, 60, pp. 465-469.
Kleiman, N. J. et al. Phosphorylation of β-crystallin B2 (βBp) in the bovine lens. The Journal of Biological Chemistry. vol. 263, No. 29, Issue of Oct. 15, 1988, pp. 14978-14983.
Kumar, A. P. et al. Elevated expression of αA-crystallins and αβ-crystallins in streptozotocin-induced diabetic rat. Archives of Biochemistry and Biophysics 444. 2005, pp. 77-83.

(Continued)

*Primary Examiner* — Chih-Min Kam
(74) *Attorney, Agent, or Firm* — Edwards Wildman Palmer LLP; Peter C. Lauro, Esq.

(57) ABSTRACT

The invention relates to the use of angiogenic crystallin proteins to promote angiogenesis, wound healing and/or endothelial cell migration. Alpha A crystallin and βB2 crystallin have particular application in these methods. The crystallins will usually be in monomeric form. Typically, truncated form(s) of βB2 crystallin protein are utilized as can be prepared by partial hydrolysis of the protein by a protease enzyme such as elastase I. Methods for the purification of crystallin proteins from eye tissue are also described.

23 Claims, 9 Drawing Sheets

OTHER PUBLICATIONS

Figure 1:
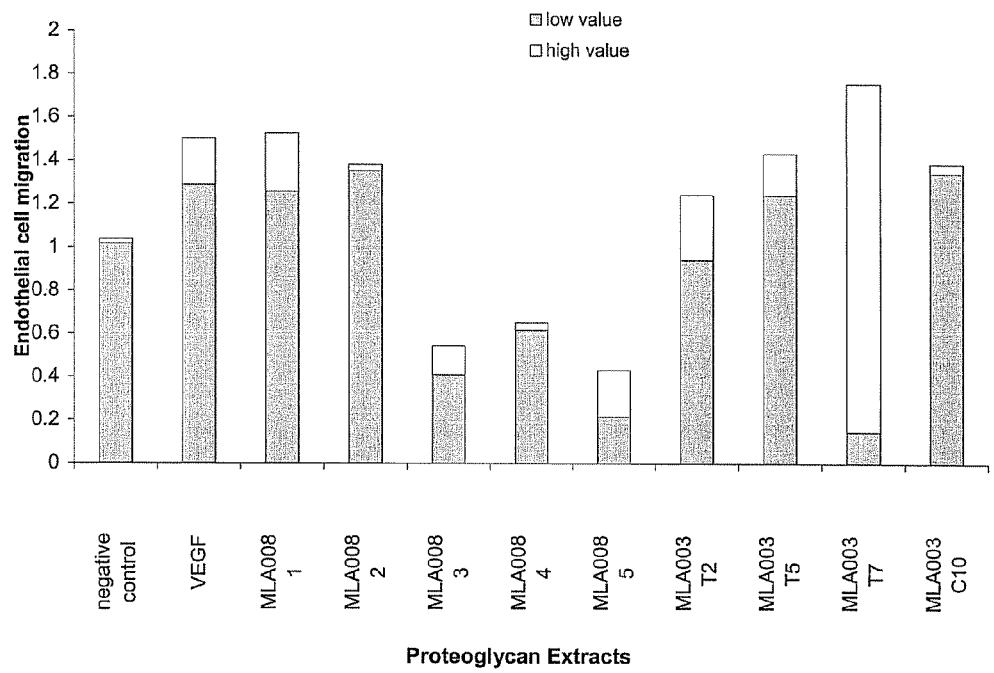

Lampi, K. J. et al. Deamidation in human lens βB2-crystallin destabilizes the dimer. Biochemistry 2006, 45, pp. 3146-3153.

Lansdown, A.B.G., (2002). Calcium: a potential central regulator in wound healing in the skin. Wound Repair and Regeneration. 10 (5), pp. 271-285.

Liu, BingFen et al. αB-crystallin inhibits glucose-induced apoptosis in vascular endothelial cells. Biochemical and Biophysical Research Communications. 321, 2004, pp. 254-258.

Liu, Bing-Fen and Liang, Jack J-N. Domain interaction sites of human lens βB2-crystallin. The Journal of Biological Chemistry. vol. 281, No. 5, Feb. 3, 2006, pp. 2624-2630.

Louapre, P. et al. Effects of hypoxia on stress proteins in the piglet heart at birth. Cell Stress & Chaperones. 2005. 10 (1), pp. 17-23.

MacCoss, M. J. et al. Shotgun identification of protein modifications from protein complexes and lens tissue. PNAS. Jun. 11, 2002, vol. 99, No. 12, pp. 7900-7905.

Magabo, K. S., et al. Expression of βB2-crystallin mRNA and protein in retina, brain and testis. Investigative Ophthalmology & Visual Science. Sep. 2000, vol. 41, No. 10, pp. 3056-X.

McFall-Ngai, M., Horwitz, J., Ding, L.-L., Lacey, L. (1986). Age-dependent changes in the heat-stable crystallin βBp, of the human lens. Current Eye Research. 5 (5), pp. 387-394.

Mellin, TN, Mennie, RJ, Cashen, DE et al (1992). Acidic fibroblast growth factor accelerates dermal wound healing. Growth Factors. 7: pp. 1-14.

Nicosia RF and Ottinetti, A. Growth of microvessels in serum-free matrix culture of rat aorta: A quantitative assay of angiogenesis in vitro. Lab Invest. 1990. 63: pp. 115-122.

Norledge, B.V. et al. The X-ray structure of a mutant eye lens βB2-crystallin with truncated sequence extensions. Protein Science. 1997, 6:1612-1620.

Ochi, Haruki et al. The stability of the lens-specific Maf protein is regulated by fibroblast growth factor (FGF)/ERK signaling in lens fiber differentiation. The Journal of Biological Chemistry. vol. 278, No. 1, Issue of Jan. 3, pp. 537-544, 2003.

Piatigorsky J., (1998). Multifunctional lens crystallins and corneal enzymes: more than meets the eye. Annals of the New York Academy of Sciences. 842, pp. 7-15.

Rutland, C.S. et al. Microphthalmia, persistent hyperplastic hyaloids vasculature and lens anomalies following overexpression of VEGF-$A_{188}$ from the αA-crystallin promoter. Molecular Vision. vol. 13, Jan. 19, 2007, pp. 47-56.

Sharma, Y. et al. Calcium ion binding to δ- and β-crystallins. The presence of the "EF-Hand" motif in δ-crystallin that aids in calcium ion binding. The Journal of Biological Chemistry. 1989. vol. 264, No. 22, Issue of Aug. 5, pp. 12794-12799.

Sharma, K. K. et al. Identification of new lens protease(s) using peptide substrates having in vivo cleavage sites. Biochemical and Biophysical Research Communications. 218, 1996, pp. 365-370.

Shearer, M. Shih et al. Identification and relative amounts of crystalline polypeptides in rat, bovine, human and chick lenses. Investigative Ophthalmology & Visual Science. Mar. 15, 1997, vol. 38, No. 4. S205—Conference Abstract.

Shimizu, T., Nomiyama, S., Hirata, F., Hayaishi, O., (1978). Indoleamine 2,3 dioxygenase. Purification and some properties. Journal of Biological Chemistry. 253 (13), pp. 4700-4706.

Smith, J.B. et al. Age related changes in young human lens crystallins. Investigative Ophthalmology & Visual Science. Mar. 15, 1997, vol. 38, No. 4. S205—Conference Abstract.

Takata, T., et al. Solvent accessibility of βB2-crystallin and local structural changes due to deamidation at the dimer interface. Experimental Eye Research. 91, 2010, pp. 336-346.

van Boekel, Martinus A.M., Lannge F.D., Grip W.F., and Jong W.W., (1999). Eye lens αA-crystallin and αB-crystallin: Complex stability versus chaperone-like activity. Biochin Biophys Acta. 1434: pp. 114-123.

van den Oetelaar, P.J.M., van Someren P.F.H.M., Thomson J.A., Siezen R.J., and Hoenders H.J., (1990). A dynamic quaternary structure of bovine K-crystallin as indicated from intermolecular exchange of subunits. Biochemistry. 29: pp. 3488-3493.

Werten, P. J. L. et al. Formation of βA3/βB2-crystallin mixed complexes: involvement of N- and C-terminal extensions. Biochimica et Biophysica Acta. 1432, 1999, pp. 286-292.

Wieligmann, K., et al. Folding and self-assembly of the domains of βB2-crystallin from rat eye lens. J. Mol. Biol. 1999, 286, pp. 989-994.

Wright, G. et al. Circular permutation of βB2-crystallin changes the hierarchy of domain assembly. Protein Science. 1998, 7:1280-1285.

Xi, Jing Hua, et al. Reduced survival of lens epithelial cells in the αA-crystallin-knockout mouse. Journal of Cell Science. 116, 2003, pp. 1073-1085.

Zhang, C. et al. A potential role for β- and γ-crystallins in the vascular remodeling of the eye. Developmental Dynamics. 2005, 234:36-47.

UniProtkB/Swiss-Prot P02522 (CRBB2_BOVIN) Jul. 22, 2008, Version 84.

Form PCT/ISA/237, Dec. 5, 2008, Written Opinion for PCT/AU2008/001319.

Form PCT/ISA/210, Dec. 5, 2008, ISR for PCT/AU2008/001319.

Ahmed, M.R. et al., "Alpha-Crystallin-Incorporated Collagen Matrices as an Aid for Dermal Wound Healing", J. Biomed. Mater. Res. Part B: Appl. Biometer., 2004, vol. 69, No. 2, pp. 241-248.

Ghosh, J.G. et al. "Interactions between Important Regulatory Proteins and Human aB Crystallin" Biochem., 2007, vol. 46, No. 21, pp. 6308-6317 ISSN: 0006-2960.

Maddala, R. & Rao, P.V. "a-Crystallin localizes to the leading edges of migrating lens epithelial cells" Exp. Cell Res., 2005, vol. 306, No. 1, pp. 203-215 ISSN: 0014-4827.

Binz, N. et al., "Long-term effect of therapeutic laser photocoagulation on gene expression in the eye" FASEB J., 2006, vol. 20, No. 2, pp. 383-385 E-ISSN: 1530-6860.

Ajaz, M.S., Ma, Z., Smith, D.L., Smith, J.B. (1997). Size of human lens β-crystallin aggregates are distinguished by N- terminal truncation of βB1. Journal of Biological Chemistry. 272 (17), pp. 11250-11255.

Behnam, K. et al. Identification of the molecular chaperone alpha B-crystallin in demineralized bone powder and osteoblast-like cells. Journal of Orthopaedic Research. 20, 2002, pp. 1190-1196.

Berbers, G.A.M. et al. Homology between the primary structures of the major bovine β-crystallin chains. Eur. J. Biochem. 139, 1984, pp. 467-479.

Berbers, G.A.M. et al. Proline- and alanine-rich N-terminal extension of the basic bovine β-crystallin $B_1$ chains. FEBS 0790. Sep. 1983, vol. 161, No. 2, pp. 225-229.

Bloemendal, Hans et al. Ageing and vision: structure, stability and function of lens crystallins. Progress in Biophysics & Molecular Biology. 86, 2004, pp. 407-485.

Brown, KJ, Maynes, SF, Bezos, A, Maguire, DJ, Ford, MD and Parrish, CR (1996). A novel in vitro assay for human angiogenesis. Lab Invest. 75: 539-555.

Chambers, C., et al. Sequence, initial functional analysis and protein-DNA binding sites of the mouse βB2-crystallin-encoding gene. Gene. 166, 1995, pp. 287-292.

Chen, C., Schultz, G.S., Bloch, M., Edwards, P.D., Tebes, S. and Mast, B.A. (1999). Molecular and mechanistic validation of delayed healing rat wounds as a model for human chronic wounds. Wound Repair & Regeneration vol. 7, No. 6, p. 486-494.

Clout, N. J. et al. The N-terminal domain of βB2-crystallin resembles the putative ancestral homodimer. J. Mol. Biol. 2000, 304, pp. 253-257.

Croft, L.R. and Waley, S.G. Structural studies on bovine γ-crystallin. Biochem. J. 1971, 121, pp. 453-459.

Dimberg, A. et al. αB-crystallin promotes tumor angiogenesis by increasing vascular survival during tube morphogenesia. Blood. vol. 111, Issue 4, Feb. 15, 2008, pp. 2015-2023.

Dirks, R.P.H., Van Genesen, S.T., Kruse, J.J.C.M., Jorissen, L., Lubsen, N.H. (1998). Extralenticular expression of the rodent βB2-crystallin gene. Experimental Eye Research. 66(2), pp. 267-269. Letter to the Editors.

Doyle, J.W., Roth, T.P., Smith, R.M., Li, Y-Q and Dunn, R.M. (1996). Effect of calcium alginate on cellular wound healing processes modelled in vitro. Journal of Biomedical Materials Research. 32, pp. 561-568.

Driessen, H.P.C. et al. Primary structure of the bovine β-crystallin Bp chain. Internal duplication and homology with γ-Crystallin. 1981. Eur. J. Biochem. 121, pp. 83-91.

Fu, Ling and Liang, Jack J.-N. Unfolding of human lens recombinant βB2- and γC-crystallins. Journal of Structural Biology. 139, 2002, pp. 191-198.

Garland, D.L. et al. Human lens crystallins in development and aging. Investigative Ophthalmology & Visual Science. Mar. 15, 1997, vol. 38, No. 4. S205—Conference Abstract.

Garrow, T.A. et al. High concentration of betaine-homocysteine methyltransferase in rhesus monkey lens. Investigative Ophthalmology & Visual Science (1997) vol. 38, No. 4 abstract 994.

Graw J. The crystallins: Genes, proteins and diseases. 1997. Biol. Chem. 378(11), pp. 1331-1348.

Hay, R.E. and Petrash J.M. Nucleotide sequence of a bovine lens αA-crystallin cDNA. Biochem. Biophys. Res. Commun. vol. 148, Issue 1, Oct. 14, 1987, pp. 31-37.

Head, Mark W. et al. βB2-crystallin in the mammalian retina. Exp. Eye Res. 1995, 61, pp. 423-428.

11164650.1, Extended European Search Report.

N. Katai et al. "Nonrefractive Role of Beta-Crystallin in the Retinal Neovascularization", Abstract, Annual Meeting of the Association-for-Research-in-Vision-and-Ophthalmology, Ft. Lauderdale, FL, USA; Apr. 24-29, 2004.

D. Sinha et al. "A Possible Function of Beta- and Gamma Crystallins in Vascular Remodeling", Abstract, Annual Meeting of the Association-for-Research-in-Vision-and-Ophthalmology, Ft. Lauderdale, FL, USA; May 1-5, 2005.

* cited by examiner

ASDHQTQAGKPQPLNPKIIIFEQ
ENFQGHSHELNGPCPNLKETGVE
KAGSVLVQAGPWVGYEQANCKGE
QFVFEKGEYPRWDSWTSSRRTDS
LSSLRPIKVDSQEHKITLYENPN
FTGKKMEVIDDDVPSFHAHGYQE
KVSSVRVQSGTWVGYQYPGYRGL
QYLLEKGDYKDSGDFGAPQPQVQ
SVRRIRDMQWHQRGAFHPSS

[1-204] mass = 23334.79

| | | | | | | |
|---|---|---|---|---|---|---|
| Small polar: | D(11) | E(14) | N(7) | Q(18) | | |
| Large polar: | K(13) | R(10) | H(8) | | | |
| Small non-polar: | S(18) | T(7) | A(8) | G(19) | | |
| Large non-polar: | L(10) | I(7) | V(14) | M(2) | F(8) | Y(9) | W(5) |
| Special: | C(2) | P(14) | | | | |

A[1] + 42.04    K[41] + 14.03    K[67] + 14.03    K[75] + 42.04
K[120] + 56.06

```
  1 A S D H Q T Q A G K P Q P L N P K I I I F E Q E N F Q G H S   30
 31 H E L N G P C P N L K E T G V E K A G S V L V Q A G P W V G   60
 61 Y E Q A N C K G E Q F V F E K G E Y P R W D S W T S S R R T   90
 91 D S L S S L R P I K V D S Q E H K I T L Y E N P N F T G K K  120
121 M E V I D D D V P S F H A H G Y Q E K V S S V R V Q S G T W  150
151 V G Y Q Y P G Y R G L Q Y L L E K G D Y K D S G D F G A P Q  180
181 P Q V Q S V R R I R D M Q W H Q R G A F H P S S              204
```

AGENTS WITH ANGIOGENIC AND WOUND HEALING ACTIVITY

This application is the U.S. national phase, pursuant to 35 U.S.C. §371, of PCT international application Ser. No. PCT/AU2008/001319, filed Sep. 5, 2008, designating the United States and published in English on Mar. 12, 2009 as publication WO 2009/029991 A1, which claims priority to Australian application Ser. No. 2007904857, filed Sep. 7, 2007. The entire contents of the aforementioned patent applications are incorporated herein by this reference.

SEQUENCE LISTING

The instant application contains a Sequence Listing which has been submitted via EFS-Web and is hereby incorporated by reference in its entirety. Said ASCII copy, created on Jul. 21, 2010, is named 85752USSequenceListinq.txt, and is 3,324 bytes in size.

FIELD OF THE INVENTION

The invention relates to the use of angiogenic crystallin proteins for promoting angiogenesis and/or wound healing. The invention also relates to compositions comprising angiogenic crystallin proteins and to processes for the purification of crystallin proteins.

BACKGROUND OF THE INVENTION

Crystallins are water-soluble proteins that are highly refractive and are related to metabolic enzymes and stress-protective proteins. Crystallins are the dominant structural components of the vertebrate eye lens and can comprise up to 90% of the protein content. The evolutionary relationships of the three classes of crystallins (α, β and γ) present in mammals have been clearly established.

There are two α crystallin genes, αA and αB (for acidic and basic, respectively), encoding proteins that share approximately 60% sequence identity. αA and αB crystallins have two domains, a crystallin domain and an alpha-crystallin-HSP domain. Two other domains share homology to the alpha-crystallin-HSP domain, namely the HSP20 domain and IbpA domain. Alpha crystallins can be induced by heat shock and are members of the small heat shock protein (sHSP) family. They act as molecular chaperones and hold unfolded or misfolded proteins in large, water soluble low molecular weight aggregates. These heterogeneous aggregates consist of 30-40 subunits of alpha crystallins in which the αA and αB subunits are present in a 3:1 ratio.

Alpha crystallins are present in all animal kingdoms but not in all organisms. Only αB crystallin has been found to be stress inducible. The expression of αA crystallin is essentially limited to the eye lens with only traces found in some other tissues. As such, αA crystallin is an essentially eye lens specific member of the family. αB crystallin is more widely expressed and is particularly abundant in brain, heart and muscle (Bloemendal et al., 2004).

β crystallins are members of the beta/gamma-crystallin family. There are at least 5 different proteins comprising the β crystallins. The beta/gamma-crystallin family of proteins contains a two-domain β-structure, folded into four very similar "Greek Key" motifs. β crystallins form homo/heterodimer, or complexes of higher order. The structure of β-crystallin oligomers appears to be stabilized through interactions between their N-terminal arms. βB2 crystallin contains a duplication of the XTALbg domain. At least 5 gamma crystallins have been identified in bovine and rat lens.

α, β and γ crystallins are the major protein components of the vertebrate eye lens with alpha crystallin being both a molecular chaperone as well as a structural protein, whilst beta and gamma crystallins are structural proteins (Bloemendal et al., 2004). Lenticular proteins, such as the abundant water-soluble crystallins cannot be replaced and thus must last the lifetime of the organism. βB2 crystallin has been demonstrated as being essential for maintaining the high solubility of crystallins in the eye lens. Its expression does not appear to be induced in other tissues upon changes in physiological condition that occur during wounding.

Proteins can be considered as evolutionarily related when conspicuous sequence similarities can be detected over longer and contiguous stretches of residues. Such homologous proteins are accordingly grouped in families and superfamilies, with higher or lower than about 50% sequence identity, respectively. Notably, there are no close structural relationships between α crystallins and the β/γ crystallins with respect to domain structure or sequence homology.

Historically, crystallins have been classified into α, β and γ classes by the size of oligmers formed that correspond with the classes now identifiable through analysis of the respective gene sequences. Whilst alpha crystallin aggregates range from 600 to 180-80 kDa and beta crystallin aggregates range from 200 to 50 kDa, the gamma crystallins are monomeric and their relative molecular mass ranges from 20 to 25 kDa (Ajaz et al., 1997; Hejtmancik et al., 1997). Beta crystallins are the most varied in aggregate size, forming several distinct classes of aggregates: β H (primarily octamers of 160-200 kDa), β L1 (primarily tetramers of 70-100 kDa and β L2 (primarily dimers 46-50 kDa) (Hejtmancik et al., 1997).

Two α crystallins αA (acidic) and αB (basic) have been described as indicated above, whereas up to 7β crystallins are known; 3 basic—B1, B2, and B3; 3 acidic—A2, A3 and A4; and the seventh form called βS. Similarly, there are several gamma crystallins (A, B, D, E, and F). Other crystallins are also known such as zeta, lambda and the heat shock proteins (hsp) hspB1 and hspB8.

The αA, βB2 and βB3 crystallins can be phosphorylated at their penultimate serine residue. Many other post-translation modifications (PTM) are also known to occur in crystallin proteins that accumulate over time as these proteins are maintained throughout the life of the animal. The PTM identified include methylation, acetylation, phosphorylation, oxidation of tyrosine and tryptophan residues, glycosylation, glutathione, and S-methylcysteine covalent attachment. A review of the types of PTM that occur in lens crystallins is provided by Hoehenwarter et al., (2006).

β crystallins are abundant lens proteins in most, if not all, vertebrate species, and have been reported in chick non-lens tissues, both ocular and extra-ocular, including the expression of βB2-crystallin in the retina (Head et al., 1991). In addition, extralenticular β crystallin expression is found in mammals and βB2 crystallin has been shown to be expressed in mouse and cat neural and pigmented retinas as well as in cat iris (Dirks et al., 1998). Although present at levels lower than those found in the lens, the appearance and accumulation of βB2 crystallin in the neural retina coincides with the functional maturation of this tissue (Head et al., 1995). βB2 expression has also been reported in bovine testes and rat brain (Magabo et al., 2000).

Extralenticular expression of βB2 indicates that it may play a metabolic role in non-lens tissues in addition to its structural role in the lens. Consistent with a possible metabolic function, βB2 is phosphorylated by cAMP-dependent kinase (PKA). Surprisingly, two forms of the protein are detected by SDS-PAGE, only one of which is phosphorylated by PKA (Kantorow and Horwitz, 1997). Incubation of recombinant mouse βB2 and bovine βB2 under identical conditions without cAMP or PKA also resulted in phosphorylation. This in vitro autophosphorylation is dependent on $Mg^{2+}$ and is serine specific. It has been shown that deletion of the βB2 C-terminal arm does not abolish autophosphorylation activity suggesting that autophosphorylation involves a different serine than the penultimate C-terminal serine identified for PKA phosphorylation.

Earlier reports identified and named a phosphorylated β crystallin protein in the eye lens as βBp (Kleiman et al., 1998). This protein was later renamed as βB2 crystallin and is synthesized in new cortical cells. The βB2 crystallin of the lens nucleus was shown to be decreased significantly in both absolute concentration and in its proportion of the total soluble protein fraction (McFall-Ngai et al., 1986). Post-translational changes in the nuclear soluble βB2 crystallin resulted in a gradual loss of approximately 3000 daltons in the apparent mass of the βBp molecule resulting in a 23 kDa protein which correlates with the relative molecular mass reported for βB2 crystallin.

International Patent Application No. PCT/US2004/014920 (WO 2005/004894) describes the treatment of conditions characterized by cell or tissue damage involving the administration of "protective proteins". Protective proteins are defined in the application as being small molecular chaperone proteins such as αA crystallin, αB crystallin, γD crystallin, Sic A, p26, and high heat stable crystallins, that improve solubility and/or stability of proteins. P26 is a low molecular weight chaperone protein of encrysted brine shrimp. SicA is another member of the small heat shock protein family and is a chaperone protein of the type III excretion system of *Salmonella*. These chaperone proteins are stated to act by protecting other proteins from damage and function by minimize degradation from conformational changes and enzymatic cleavage or digestion, thereby enhancing cell and tissue viability. The properties of the protective proteins are stated to include enhancing wound healing.

International Patent Application No. PCT/JP2004/00609 (WO 2004/096277) relates to the use of a preventative or therapeutic agent for intraocular vascularisation disease. The agent is stated to be a crystallin inhibitory substance, and can comprise an antisense RNA oligonucleotide having a nucleotide sequence complementary to a sequence coding for βB2 crystallin. In particular, an animal model is described in which βB2 crystallin is expressed in or around retinal vasculature induced with exposure of the retina to high levels of oxygen. High oxygen conditions are important for propyl hydroxylase activity to form hydroxyproline in collagen, and the observation of the expression of βB2 crystallin is consistent with a structural role for the protein.

Any break in the skin, regardless of the cause gives bodily access to foreign pathogens, providing a fertile breeding ground and a potential site for serious infection that may become life threatening. Both acute and non-healing chronic wounds remain a challenge in terms of both treatment and to the health care system. As such, there is an ongoing need for improved treatments for acute and chronic wounds which often require intensive and costly treatments.

SUMMARY OF THE INVENTION

Broadly stated, the invention stems from the surprising observation that certain mammalian crystallin proteins have angiogenic activity and can promote endothelial cell proliferation and/or migration. Hence, the invention in one or more forms extends though not exclusively, to the treatment of wounds and the promotion of wound healing.

More particularly, in one aspect of the invention there is provided a method for promoting angiogenesis in a subject in need thereof, comprising treating the subject with an effective amount of at least one angiogenic crystallin protein.

In another aspect of the invention there is provided a method for promoting endothelial cell proliferation and/or migration in a subject in need thereof, comprising treating the subject with at least one angiogenic crystallin protein.

Any angiogenic crystallin protein can be utilised to promote angiogenesis or endothelial cell proliferation and/or migration in accordance with a method embodied by the invention. In at least some forms, the angiogenic crystallin protein is an αA crystallin protein, or an angiogenic fragment of αA crystallin or βB2 crystallin. Surprisingly, it has been found that while intact (e.g., undigested) βB2 crystallin has no angiogenic activity, truncated forms of this crystallin protein as may be provided by partial enzymatic digestion promote angiogenesis (i.e, are angiogenic). Enzymes such as elastase and other proteases are present/released at wound sites and hence, while intact βB2 crystallin itself has no effect on angiogenesis or wound healing, the intact protein can be administered for cleavage at the wound or treatment site to release truncated active form(s) of the protein. As such, intact βB2 crystallin has application in embodiments of the invention. Moreover, angiogensis and endothelial cell migration are important components of the wound healing mechanism, and βB2 crystallin protein with angiogenic activity also has application in wound healing and promoting endothelial cell as described herein.

Accordingly, in another aspect of the invention there is provided a method for treating a wound in a subject, comprising administering an effective amount of at least one βB2 crystallin protein to the subject.

In another aspect of the invention there is provided a method for promoting wound healing in a subject, comprising administering an effective amount of at least one βB2 crystallin protein to the subject.

In another aspect there is provided a pharmaceutical composition for use in a method embodied by the invention, comprising at least one βB2 crystallin protein, together with a pharmaceutically acceptable carrier.

In another aspect of the invention there is provided the use of at least one crystallin protein for promoting angiogenesis in a subject.

In another aspect of the invention there is provided the use of at least one crystallin protein for promoting endothelial cell proliferation and/or migration in a subject.

In another aspect of the invention there is provided the use of at least one βB2 crystallin protein for treating a wound or promoting wound healing in a subject.

The crystallin protein can administered directly to target tissue or a wound site. For the treatment of skin and open wounds, the crystallin protein can be administered in a topically acceptable carrier.

Moreover, the invention extends to a process for the purification of crystallin proteins. Accordingly, in another aspect of the invention there is provided a process for the purification of at least one crystallin protein, comprising:

(a) removing the lens sheath of an eye lens obtained from the carcass of an animal, the removal of the lens sheath leaving remaining lens tissue of the eye lens;

(b) placing the lens tissue in an aqueous solvent for a period of time to dissolve the crystallin protein from the tissue into the solvent; and (c) recovering the crystallin protein from the solvent.

In at least some forms, the method will further comprise removing un-dissolved lens tissue from the solvent prior to recovering the crystallin protein from the solvent.

The method of purification can also comprise providing the lens tissue by slicing the eye to form an incision in the eye, and applying pressure to the eye to force the lens from the eye through the incision. The lens sheath will normally be removed prior to soaking the lens in the solvent. The solvent can also be acidified to assist in the dissolution of the crystallin protein from the lens tissue. Thus, the method of purification can further include lowering the pH of the solvent to pH 5.0 or less after the lens tissue has been in the solvent for an initial predetermined interval. The dissolution of the crystallin protein can occur in the absence of the addition of any protease or digestive enzymes to the solvent. That is, the solvent in which the lens tissue is placed can be free of any such enzymes. Any suitable chromatography technique can be used to recover the crystallin protein from the solvent. The solvent will typically be water.

In another aspect of the invention there is provided a method for purifying one or more crystallin proteins from the lens of an eye of a carcass of an animal, comprising:

(a) slicing the eye to form at least one incision in the eye;

(b) applying pressure to the eye forcing the lens from the eye through the incision;

(c) dissolving the crystallin protein from the lens into a solvent; and (d) purifying the crystallin protein from the solvent.

In at least some forms, the incision will be made between the sclera and pupil of the eye. The eye can be separated from the carcass of the animal prior to the removal of the lens, or it can be removed from the eye while the eye remains in position in the carcass. The crystallin protein can purified from the solvent by chromatographic separation (e.g., on a C4 RP-HPLC column) or other suitable separation technique.

The crystallin protein utilised in accordance with the invention can be of invertebrate or mammalian origin, for example, human, bovine, ovine, porcine or caprine crystallin protein. In at least some embodiments, mammalian crystallin protein is utilised. The crystallin protein will typically be in monomeric form. The monomeric form can consist of truncated or protease cleaved form(s) of the crystallin protein.

The term "crystallin protein" in the context of the invention encompasses native crystallin protein, as well as angiogenic truncated (e.g., fragments), and modified forms of the protein, that essentially retain the angiogenic and/or wound healing activity of the protein. Particularly suitable truncated forms include those comprising the globular domain or one or more (typically all) of "Greek key" domains as can be provided by partial digestion of the protein with a suitable protease such as elastase I or chymotrypsin.

The phrases "acceleration or promotion of wound healing" "or promoting angiogenesis" as used herein refers to enhancement of the wound healing process, angiogenesis or a stage thereof by the administration of the crystallin protein or angiogenic fragment of the protein.

The term "protein" is used herein interchangeably with "peptide" unless the context in which it is used states or requires otherwise.

The subject treated by a method embodied by the invention can be a mammal such as, for example, a member of the bovine, porcine, ovine or equine families, a laboratory test animal such as a mouse, rabbit, guinea pig, a cat or dog, or a primate or human being.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated in their entirety by reference. Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed in Australia or elsewhere before the priority date of this application.

The features and advantages of the invention will become further apparent from the following detailed description of non-limiting embodiments together with the accompanying drawings.

BRIEF DESCRIPTION OF THE ACCOMPANYING DRAWINGS

FIG. 1: Graph showing endothelial cell migration results for MLA008E2 proteoglycan extract of bovine eye.

Figure 2:
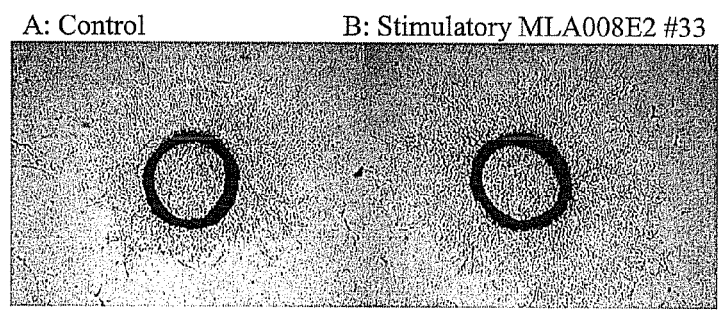

FIG. 2: Photomicrograph showing the effects on endothelial cell migration and proliferation of a (A) control and (B) MLA008E2 proteoglycan extract in a rat aortic ring angiogenesis assay.

Figure 3:
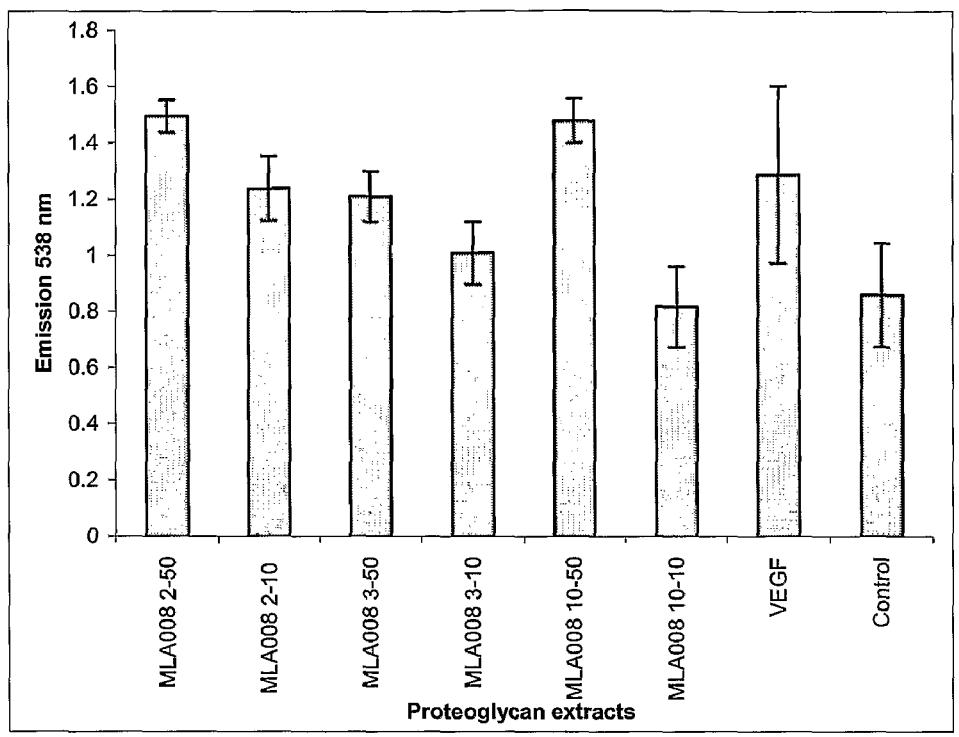

FIG. 3: Graph showing the endothelial cell migration activity by extract MLA008E2.

Figure 4A:
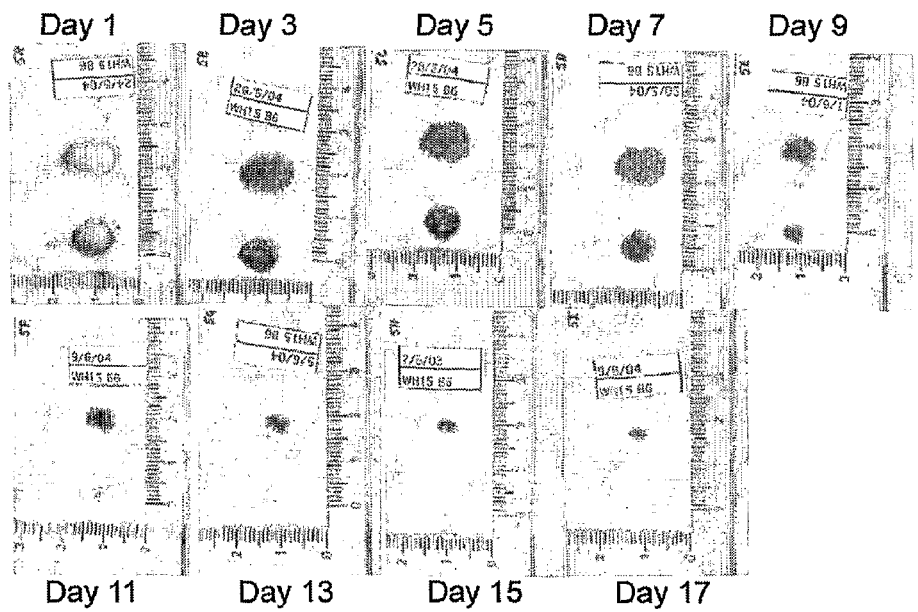

FIG. 4: (A) Photographs showing the size of treated wounds compared to control wound size over a 17 day period. (B) Graph showing decrease in wound size over the above test period.

Figures 4B, 5:
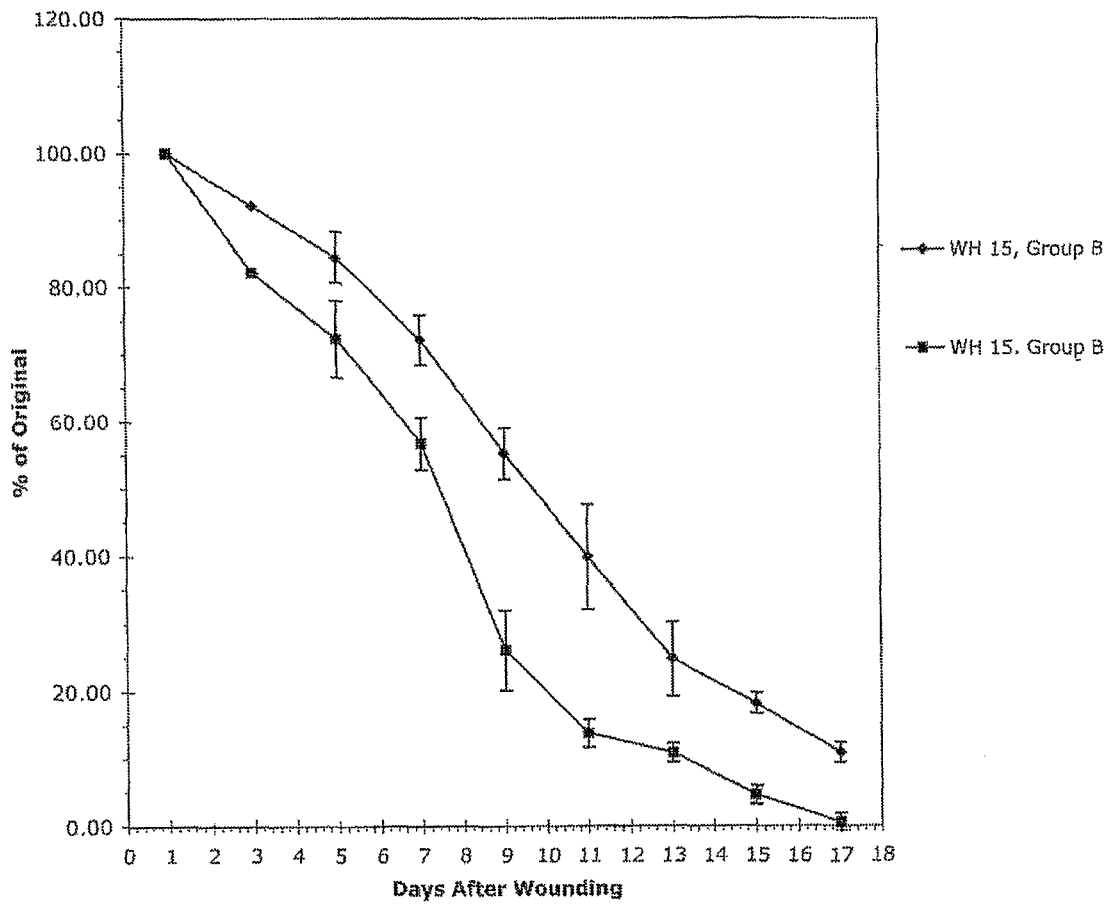

FIG. 5: Amino acid sequence of bovine βB2 crystallin protein (SEQ ID No.1).

Figure 6:
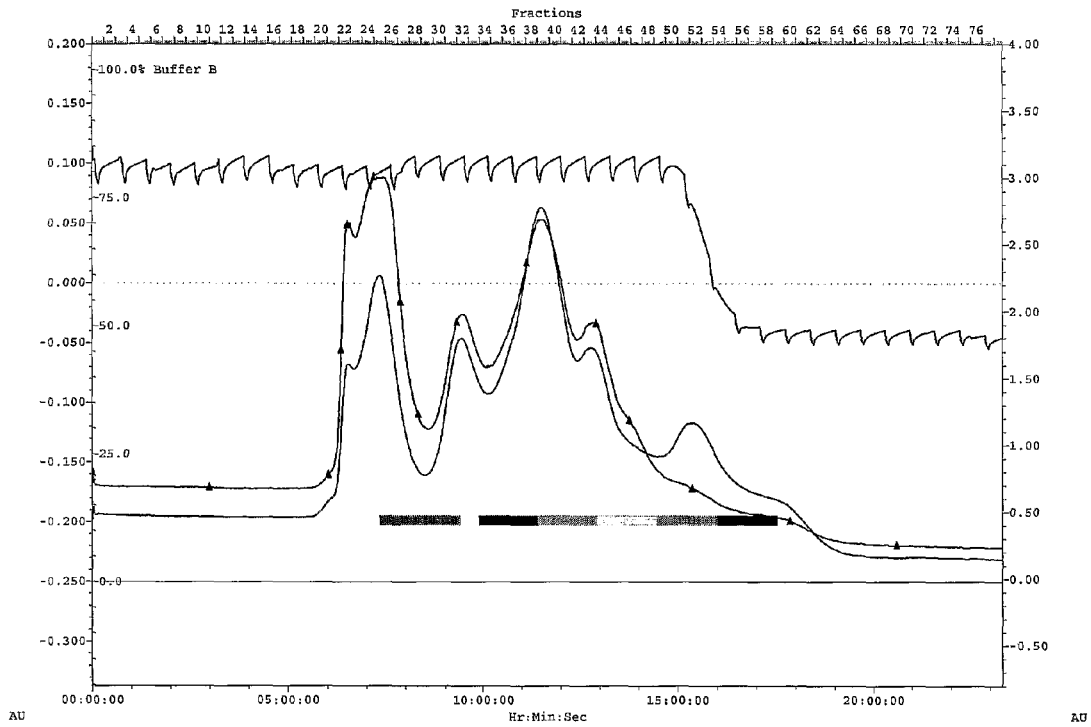

FIG. 6: Elution profile for bovine crystallin extract (6 mL) on a 1 L Sephacryl 300 HR column. The zigzag line represents the conductivity. Fractions collected are indicated across the top of x-axis. Alpha A and B crystallin (Fractions 20-28), β H crystallin (Fractions 29-33), β L1 (Fractions 34-41), β L2 (Fractions 42-45), gamma S (Fractions 46-49) and gamma BC/DE (Fractions 50-56).

Figure 7:
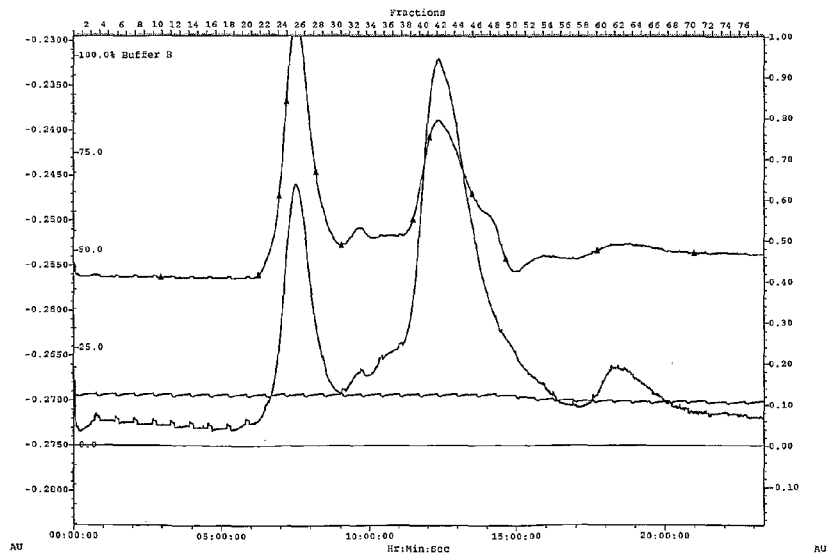

FIG. 7: Elution profile for bovine crystallin extract adjusted to pH 5.0 (25 mL) on a 1 L column Sephacryl 300 HR. Fractions collected are shown (18 mL) across the top of x-axis.

Figures 8, 9:
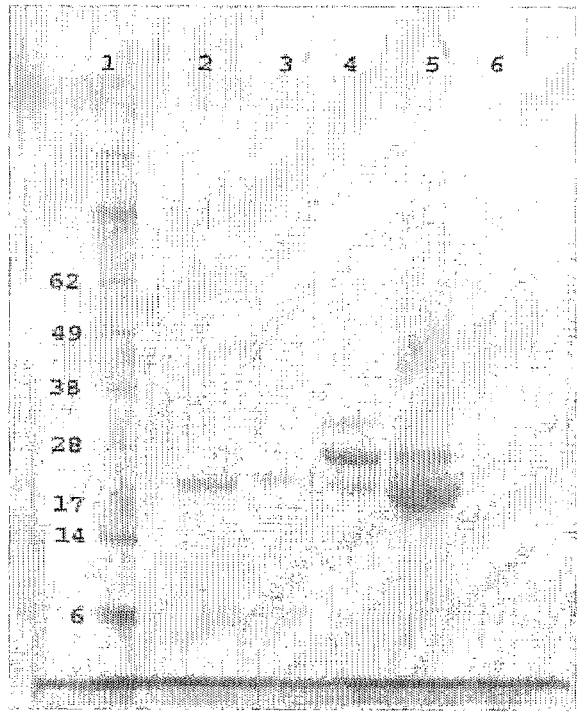

FIG. 8: SDS PAGE analysis of bovine crystallin fractions eluted from DEAE Sepharose. Lane 1: MW Markers, Lane 2: Fractions 21-34, Lane 3: Fractions 37-47, Lane 4: Fractions 50-60, Lane 5: Fractions 61-77.

Figure 10:
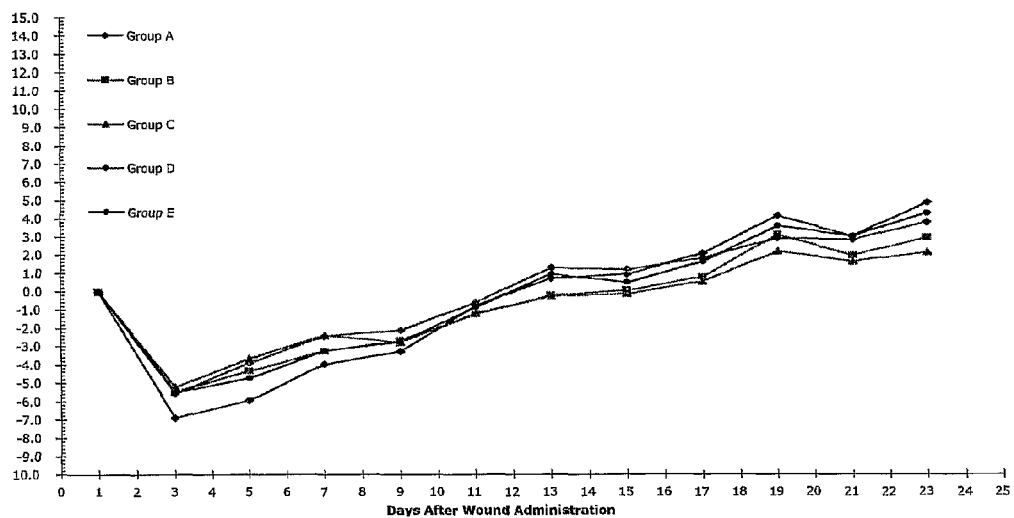

FIG. 9: βB2 amino acid sequence (SEQ ID No.1) indicating possible post-translational modifications to the protein FIG. 10: Graph showing average weight gain of rats over the period of a wound healing study. Group A: Vehicle control phosphate buffered saline. Group B: Wound Heal 1 low protein concentration (0.01 mg/wound) βB2 crystallin. Group C: Wound Heal 2 high protein concentration (0.1 mg/wound) βB2 crystallin. Group D: Wound Heal 3 (1.0 mg/mL) αB crystallin. Group E: Positive control Aloe Vera gel (20 mg/wound).

Figure 11:
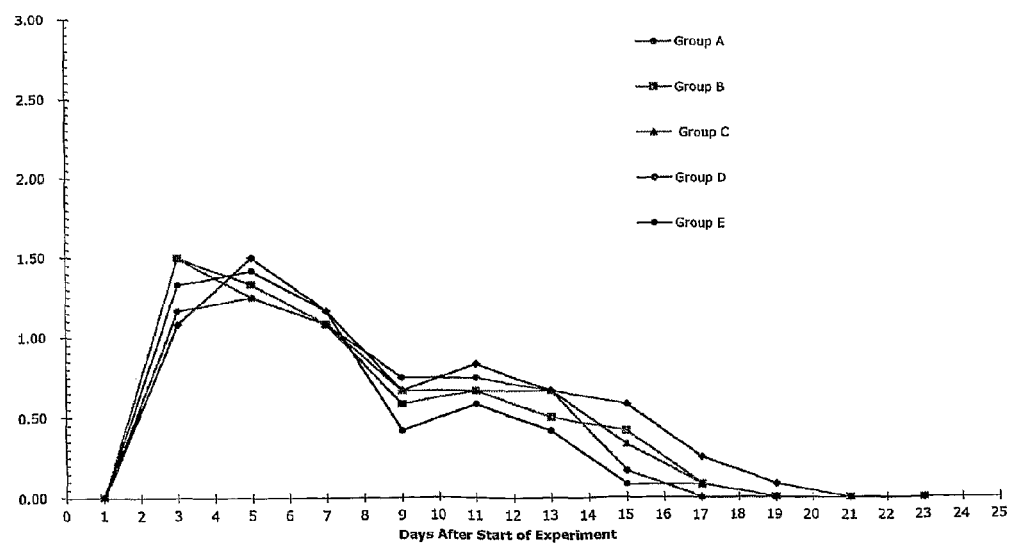

FIG. 11: Graph showing inflammatory response during the course of wound healing.

Figure 12:
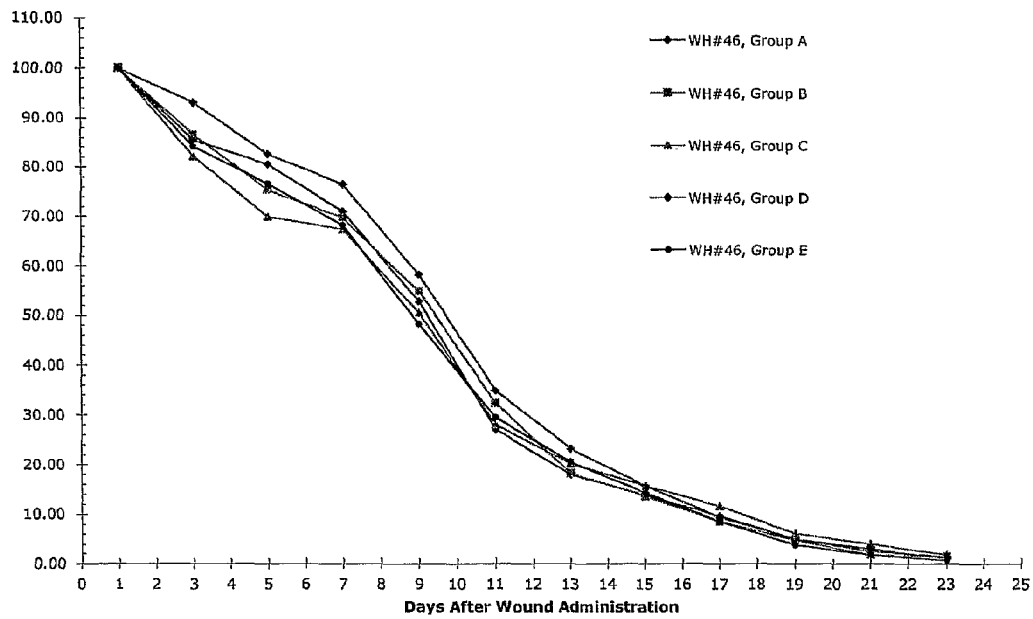

FIG. 12: Graph showing comparison of wound healing closure rates. Group A: Vehicle control phosphate buffered saline. Group B: Wound Heal 1 low protein concentration (0.01 mg/wound) βB2 crystallin. Group C: Wound Heal 2 high protein concentration (0.1 mg/wound) βB2 crystallin.

Group D: Wound Heal 3 (1.0 mg/mL) αB crystallin. Group E: Positive control Aloe Vera gel (20 mg/wound).

Figure 13:
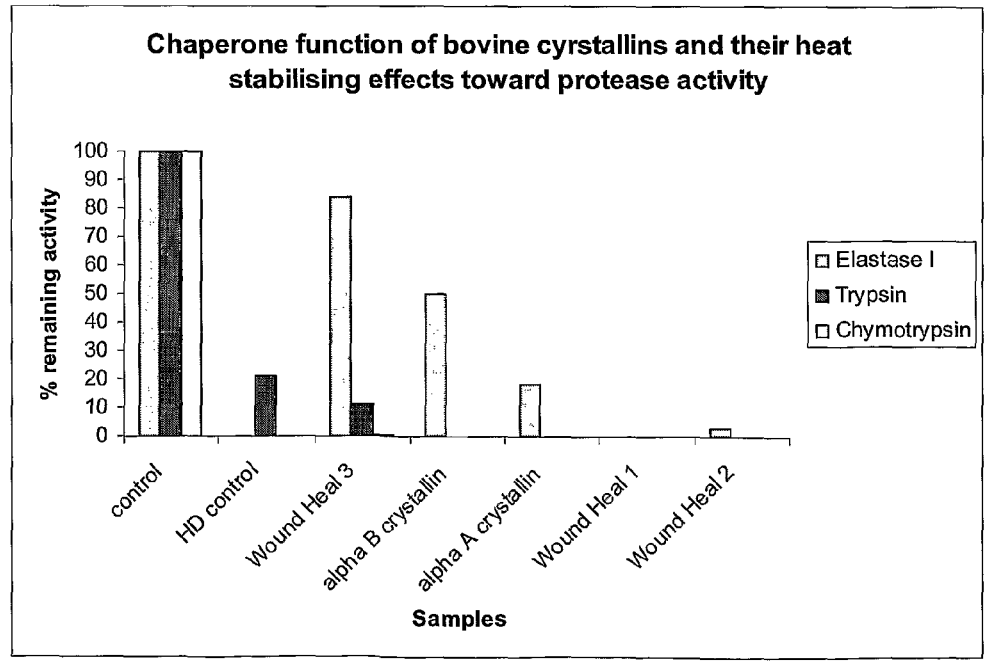

FIG. 13: Graph indicating chaperone activity of bovine crystallin fractions to protect against heat degradation of various proteases.

Figure 14:
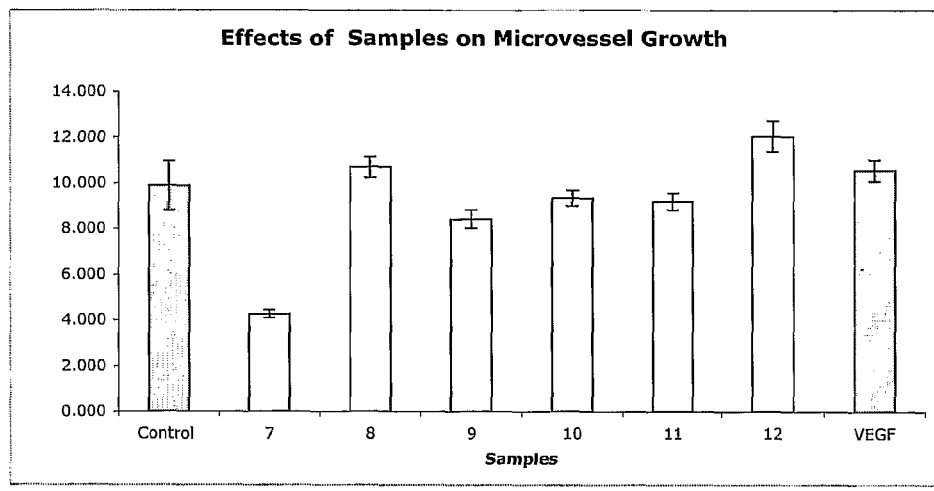

FIG. 14: Graph indicating angiogenesis potential of bovine crystallin proteins. Sample 7: Bovine βB3 crystallin (prepared by bovine crystallin heat denaturation at 97-99° C. for 3 minutes, supernatant collected by centrifugation). Sample 8: Bovine αA crystallin. Sample 9: Bovine αB crystallin. Sample 10: Wound Heal 1 bovine βB2 crystallin (prepared by fractionated at pH 5.3 using Sephacryl 300 HR fractions 40-48). Sample 11: Wound Heal 3 bovine αB crystallin (Bovine α crystallin extract fractionated on DEAE Sepharose fast flow fractions 37-47). Sample 12: Wound Heal 2 bovine βB2 crystallin (prepared by ultra filtration, 100 kDa retentant Sephacryl 300 HR fractions 40-48.

Figure 15:
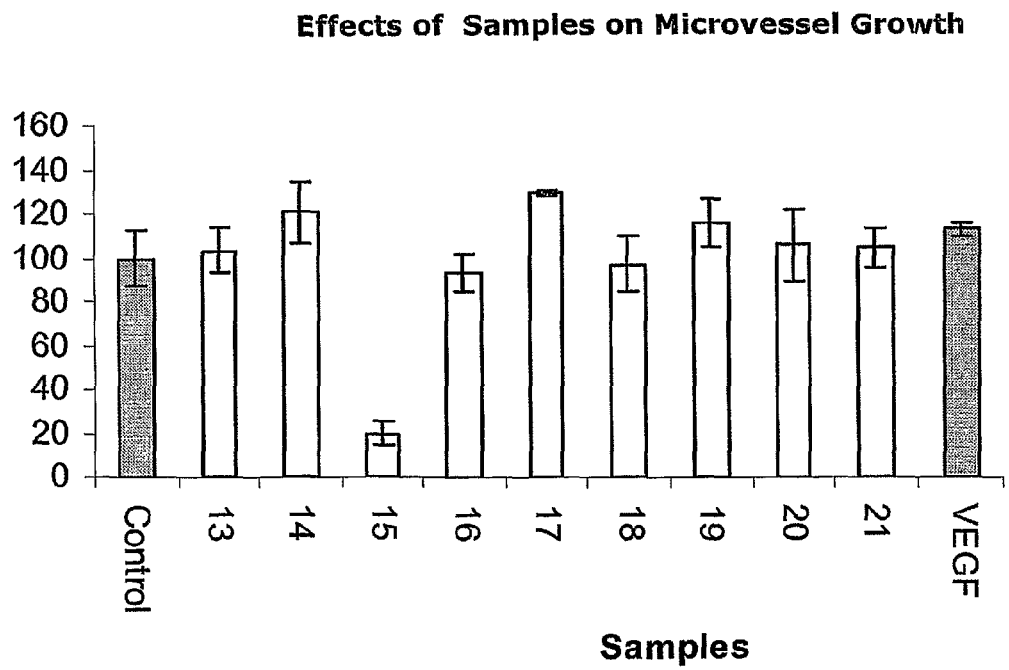

FIG. 15: Graph indicating angiogenesis potential of bovine crystallin proteins

Sample 13: Ovine βB2 crystallin (prepared by RP HPLC on C4 column). Sample 14: βB2 crystallin treated with elastase I. Sample 15: Bovine βB2 crystallin (prepared by RP HPLC on C4 column). Sample 16: Ovine αA crystallin. Sample 17: Ovine αB crystallin. Sample 18: Indoleamine 2,3-dioxygenase. Sample 19: Tryptophan dioxygenase. Sample 20: Indoleamine 2,3-dioxygenase and ovine βB2 crystallin. Sample 21: Tryptophan dioxygenase and ovine αB crystallin.

Figure 16:
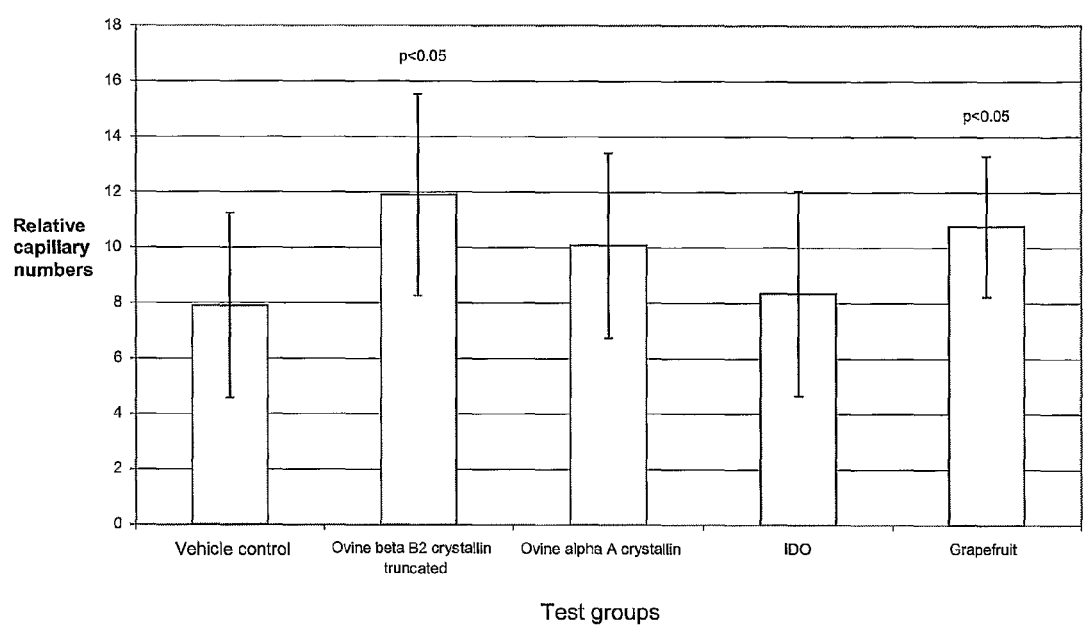

FIG. 16: Graph of capillary blood vessel density in the transition zone between normal skin and wounds treated with an elastase I truncated form of βB2 crystallin compared to a vehicle only control.

DETAILED DESCRIPTION OF EXEMPLARY EMBODIMENTS OF THE INVENTION

The angiogenic activity and/or endothelial cell proliferative or migration potential of a crystallin protein can be assessed by assays and methodology described herein or as otherwise deemed appropriate by the skilled addressee. The crystallin protein can be any vertebrate or mammalian crystallin, and may be a native crystallin, or a recombinant or other synthetic protein. The amino acid sequence for bovine αA crystallin is for instance provided by GenBank Accession No. NP_776714 crystallin, alpha A [Bos taurus]. The amino acid sequence identity of αA cystallin for example is highly conserved between species with bovine αA cystallin having 98% amino acid sequence identity with mouse, hamster and rat αA cystallin (Hay and Petrash., 1987). The amino acid sequence for bovine βB2 crystallin is for instance provided by (GenBank accession No. NM_174807 Bos taurus crystallin, beta B2 (CRYBB2), mRNA.

The animal from which native crystallin protein is purified can for instance be a member of the bovine, ovine, porcine, equine, canine, feline, primate, rodent or other mammalian family. In at least some forms, the crystallin protein will be a bovine or ovine crystallin protein. Typically, the crystallin protein will be purified from eye lens. Ovine and bovine eye lens is particularly suitable.

A recombinant crystallin protein can have an identical amino acid sequence to the native crystallin or one or more amino acid differences compared to the native protein. The amino acid changes can comprise the addition, deletion and/or substitution of one or more amino acids. Inversion of amino acids and other mutational changes that result in modification of the native crystallin protein sequence are also encompassed. Moreover, a recombinant protein can comprise an amino acid or amino acids not encoded by the genetic code. For example, D-amino acids rather than L-amino acids can be utilized to inhibit endopeptidase degradation of the protein in vivo.

The substitution of an amino acid can be a conservative or non-conservative substitution. The term conservative amino acid substitution is to be taken in the normally accepted sense of replacing an amino acid residue with another amino acid having similar properties which substantially does not adversely affect the angiogenic and/or wound healing activity of the crystallin protein. For example, a conservative amino acid substitution can involve substitution of a basic amino acid such as arginine with another basic amino acid such as lysine. Likewise, for instance a cysteine residue can be replaced with serine, or a non-polar amino acid may be substituted with another non-polar amino acid such as alanine. Amino acids amenable to substitution or deletion in a crystallin protein amino acid sequence may be determined by comparison of the sequence with closely related crystalline proteins to identify non-conserved amino acids and by routine trial and experimentation well within the skill of the addressee. A modified recombinant crystallin protein can be provided by introducing nucleotide change(s) in nucleic acid sequence encoding the native protein such that the desired amino acid changes are achieved upon expression of the nucleic acid in a host cell.

A recombinant or other synthetic crystallin protein useful in a method embodied by the invention will have amino acid sequence identity with the native crystallin of about 60% or greater, and more usually at least about 70%, 80%, 90%, 95%, 98% or greater, or 100%, and all sequence homologies and ranges thereof within those enumerated above are expressly encompassed. Sequence identity between amino acid sequences is determined by comparing amino acids at each position in the sequences when optimally aligned for the purpose of comparison. The sequences are considered identical at a position if the amino acids at that position are the same. A gap, that is a position in an alignment where an amino acid residue is present in one sequence but not the other is regarded as a position with non-identical residues. Alignment of sequences may be performed using any suitable program or algorithm such as for instance, by the Needleman and Wunsch algorithm (Needleman and Wunsch, 1970). Computer assisted sequence alignment can be conveniently performed using standard software programs such as GAP which is part of the Wisconsin Package Version 10.1 (Genetics Computer Group, Madison, Wis., United States) using the default scoring matrix with a gap creation penalty of 50 and a gap extension penalty of 3.

The crystallin protein can also be chemically synthesized. The provision and use of fusion proteins incorporating a crystallin protein as described herein is also expressly encompassed by the invention. Nucleic acid encoding a fusion protein can be provided by joining separate DNA fragments encoding the crystallin protein and, for example, a lipophilic amino acid sequence for enhancing the lipophilic characteristics of the protein by employing blunt-ended termini and oligonucleotide linkers, digestion to provide staggered termini and ligation of cohesive ends as required. Techniques for providing recombinant and fusion proteins as described herein are well known to the skilled addressee (eg., see also Ausubel et al. (1994) Current Protocols in Molecular Biology, USA, Vol. 1 and 2, John Wiley & Sons, 1992, Sambrook et al (1998) Molecular cloning: A Laboratory Manual, Second Ed., Cold Spring Harbour Laboratory Press, New York, and subsequent editions and updates of the foregoing), the contents of which are incorporated herein in their entirety by cross-reference.

Host cells that can be transfected for expression of recombinant crystallin proteins and fusion proteins as described herein include bacteria such as *E. coli, Bacillus* strains (eg., *B. subtilis*), *Streptomyces* and *Pseudomonas* bacterial strains, yeast such as *Sacchromyces* and *Pichia*, insect cells, avian cells and mammalian cells such as Chinese Hamster Ovary cells (CHO), COS, HeLa, HaRas, WI38, SW480, and NIH3T3 cells. The host cells are cultured in a suitable culture medium under conditions for expression of the introduced nucleic acid (typically in an appropriate expression vector) prior to purification of the expressed product from the host cells, and/or supernatants as required using standard purification techniques known in the art or as described herein.

Crystallin proteins as described herein can also be modified by coupling one or more proteinaceous or non-proteinaceous moieties to the protein to improve solubility, lipophilic characteristics, stability, biological half-life, or for instance to act as a label for subsequent detection or the like. Modifications can also result from post-translational or post-synthesis modification such as by the attachment of carbohydrate moieties, or chemical reaction(s) resulting in structural modification(s) (eg., the alkylation or acetylation of one or more amino acid residues or other changes involving the formation of chemical bonds). In particular, the crystallin protein can have one or more modifications selected from the group consisting of methylation, phosphorylation, oxidation of tyrosine and/or tryptophan residues, glycosylation, and S-methylcysteine covalent attachment.

Further, the crystallin protein may be pegylated or ornithinylated to render it less resistant to degradation by proteases in vivo or to inhibit their clearance from the circulation via the kidneys. Methods such as pegylation of peptides are well known in the art and all such modifications are expressly encompassed.

The crystallin protein can be of a size with a range of from about 16 Da to about 32 Da. In particular, an αA crystallin protein will normally be of a size in a range of from about 16 Da to about 20 Da, and more usually in a range of from about 18 Da to about 20 Da. A βB2 crystallin protein employed in one or more methods embodied by the invention will normally be of a size in a range of from about 15 Da to about 28 Da and more usually, in a range of from about 20 Da to about 25 Da.

C-terminal and N-terminal extensions of native crystallin proteins are involved in stabilization of quaternary structure and the generation of aggregates of the protein. Thus, crystallins lacking such C-terminal and N-terminal extensions forms aggregates poorly. Alpha crystallins form large aggregates. They have a heat shock domain and as with beta crystallins, have extensions at the N terminus involved in aggregate formation. Electrostatic interactions between crystallin proteins are also involved in crystallin aggregate formation, and ionization of histidine residues below a pH of 5 can disrupt the aggregates. Typically, the crystallin protein used in a method embodied by the invention will be in monomeric form. Crystallin monomers can be prepared by partial hydrolysis (e.g., by partial protease digestion such as by elastase or chymotrypsin) of extracted crystallin protein such that the native C-terminal and/or N-terminal extensions of the protein are removed leaving in the case of at least βB2 crystallin, the globular central core or "globular domain or Greek key motifs". The globular domain of the crystallin protein exhibits angiogenic and/or endothelial cell proliferative or migration potential. Fragments of αA crystallin employed in methods embodied by the invention will normally comprise the crystallin and heat shock domains of the protein.

As examples, the N-terminal end of βB2 crystallin can be cleaved by elastase I (i.e., ASDHQTQA/GKPQPLNPKII (SEQ ID No. 2) with the cleavage point being indicated by "/" to yield cleavage products ASDHQTQA (SEQ ID No. 6) and GKPQPLNPKII (SEQ ID No. 7)) as can the C-terminal end of the protein (RDMQ WHQRGA/FHPSS (SEQ ID No. 3) to yield cleavage products RDMQ WHQRGA (SEQ ID No. 8) and FHPSS (SEQ ID No. 9)) resulting in truncated forms of βB2 crystallin having application in one or more embodiments of the invention. In particular, truncated forms of βB2 crystallin that may be used include the domain comprising amino acids 17 to 191 of Swiss Prot accession number P02522 (UniProtKB/Swiss-Prot P02522 (CRBB2_Bovin); www.uniprotorg/uniprot/P02522), and those consisting or comprising amino acids 2 to 200 and 10 to 200 of Swiss Prot accession number P02522. Moreover, an angiogenic βB2 cystallin protein can comprise one or more (typically all) of the "Greek key" domains of the protein, such as amino acids 17-56 (Greek key 1), 57-101 (Greek key 2), 107-148 (Greek key 3) and 149-191 (Greek key 4) of Swiss Prot accession number P02522.

The intact and truncated forms of a crystallin protein useful in embodiments of the invention may be subjected to post translational modifications not limited to acetyl, methyl, ethyl, phosphorylation, oxidation and glycosylation modifications in the native crystallin protein. For example, the following amino acids of βB2 crystallin (e.g., see Swiss Prot accession number P02522) can be modified as follows (AA indicates amino acid position): AA2 N-acetylalanine; AA42 N6-methylated lysine; AA68 N6-methylated lysine; AA76 N6-acetyllysine; AA118 phosphothreonine; AA121 N6-acetyllysine or N6-methylated lysine; AA11 N-(Glc); AA48 N-(Glc); AA68 N-(Glc); AA76 N-(Glc); AA101 N-(Glc); AA108 N-(Glc); AA120 N-(Glc); AA121 N-(Glc); AA140 N-(Glc); AA168 N-(Glc) and AA172 N-(Glc). Typically, intact (undigested) αA crystallin will be utilised in embodiments of the invention as described herein. Most usually, the αA crystallin protein will be unmodified or at least non-phosphorylated (as may be achieved by treatment of native protein with alkaline phosphatase). Suitable conditions for alkaline phosphatase activity include suitable zinc, magnesium or calcium containing buffers with a pH in a range of from about 8.0 to 9.8.

Partially hydrolysed forms of crystallin proteins can be purified for use in embodiments of the invention by any suitable purification technique including, but not limited to filtration and chromatography (e.g., RP-HPLC) protocols.

Tissue sites and wounds that may be treated in accordance with the invention include acute and chronic wounds, burns including burns arising from exposure to ionizing radiation, chemical wounds, surgical wounds, oral wounds, skin and muscle trauma, open skin wounds, diabetic skin sores including diabetic foot ulcers, diabetic naturopathic foot ulcers, ischemic tissue including ischemic naturopathic foot ulcers, venous stasis ulcers, pressure sores, and hypoxic tissue. Examples of ischemic and hypoxic tissues include ischemic heart tissue and hypoxic tissues associated with stroke. Conditions in which the wound healing process may be promoted by the administration of the crystallin protein include in circumstances of delayed wound healing in which healing is impaired or prevented by for example, tissue hypoxia, repeated trauma, or systemic causes such as diabetes and vascular disease.

Examples of endothelial cell types that may be induced to proliferate and/or migrate by crystallin proteins in accordance with the invention include human umbilical vein endothelial cells, human microvascular endothelial cells, and bovine aorta endothelial cells.

The crystallin protein can be administered to a subject in need of such treatment alone or be co-administered with one or more other therapeutic agents. For example, the crystallin protein can be co-administered in combination with therapeutic agents conventionally used for promoting angiogenesis and/or wound healing. By "co-administered" is meant simultaneous administration in the same formulation or in two different formulations by the same or different routes, or sequential administration by the same or different routes, whereby the crystallin protein and other therapeutic agent(s) exhibit overlapping therapeutic windows. By "sequential" administration is meant one is administered after the other. Such further agents that may be co-administered with the crystallin protein include platelet-derived growth factor (PDGF), transforming growth factor-$\beta$ (TGF-$\beta$), platelet-derived wound healing factor, insulin growth factor (IGF), keratinocyte growth factor (KGF), anti-inflammatory agents and anti-microbial agents. Further examples of other therapeutic agents used for promoting angiogeneisis and/or wound healing that may be co-administered with the crystallin protein include indoleamine 2,3-dioxygenase (IDO), tryptophan dioxygenase (TDO), spingosine-1-phosphate (SIP), N-acyle-thanolamines, grapefruit extract and other plant phytochemicals including ascein, green tea catechins, melatonin, arginine and other amino acids for support of vessel growth.

The crystallin protein will generally be formulated into a pharmaceutical composition comprising the protein and a pharmaceutically acceptable carrier. Suitable pharmaceutical compositions include topically acceptable formulations such as creams, lotions, ointments and gels for internal or external application. Topically acceptable compositions can be applied directly to the site of treatment including by way of dressings and the like impregnated with the preparation. Gels comprising a crystallin protein precipitate are particularly suitable. Gels and other pharmaceutical compositions as described herein may also include calcium ions and/or salts. The presence of calcium in the composition can enhance wound healing.

A pharmaceutical composition as described herein can also incorporate one or more preservatives such as parabens, chlorobutanol, and sorbic acid, binders such as corn starch or gelatin, thickening agents, emulsifiers, surfactants, gelling agents, and other components typically used in such compositions. Pharmaceutically acceptable carriers include any suitable conventionally known topically and physiologically acceptable solvents, dispersion media, isotonic preparations and solutions. Use of such ingredients and media for pharmaceutically active substances is well known. Except insofar as any conventional media or agent is incompatible with the crystallin protein, use thereof is expressly encompassed.

Pharmaceutical compositions embodied by the invention include therapeutic compositions for human or veterinary use. Typically, the pharmaceutical composition will have a pH suitable for application of the composition directly to a wound. Generally, the pH will be above 3.8 and usually, about 4 or higher. Crystallin protein precipitate gels as described herein can precipitated from a solution containing the protein and a physiologically acceptable buffer system such that the precipitate has the desired pH. Alternatively, the pH of the gel can be altered to the desired pH by the addition of any suitable pH modifier(s) to the gel.

A pharmaceutical composition embodied by the invention will generally contain at least about 0.001% by weight of the crystallin protein up to about 80% w/w of the composition. For example, the pharmaceutical composition can contain about 0.05%, 0.01%, 0.1%, 1%, 10%, 20%, 30%, 40%, 50%, 60%, 70%, or 80% by weight of the crystallin protein. The amount of the protein in the composition will be such that a suitable effective dosage will be delivered to the subject taking into account the proposed mode of administration.

The dosage of the crystallin protein administered in accordance with an embodiment of the invention will depend on a number of factors including whether the protein is to be administered for prophylactic or therapeutic use, the disease or condition for which the protein is intended to be administered, the severity of the condition, the sex and age of the subject, and related factors including weight and general health of the subject, and can be determined in accordance with accepted medical principles. For instance, a low dosage can initially be given which is subsequently increased at each administration following evaluation of the subject's response. Similarly, the frequency of administration can be determined in the same way that is, by continuously monitoring the subject's response between each dosage and if desirable, increasing the frequency of administration or alternatively, reducing the frequency of administration.

Typically, the crystallin protein will be administered in accordance with a method embodied by the invention at a dosage up to about 50 mg/kg body weight and preferably, in a range of from about 5 µg/kg to about 100 µg/kg body weight. For topical application, the crystallin protein will be administered to a tissue or wound site in a dose range of about 0.1 µg to 100 µg/cm$^{-1}$. The dose administered topically can be about 0.1, 0.5, 1.0, 5.0, 10, 20, 30, 40, 50, 60, 70, 80, 90 or 100 ug/cm$^{-1}$. Typically, the protein will be administered at a dosage in a range of from 1.0 to 10.0 µg/cm$^{-1}$ of the tissue to be treated.

Routes of administration include but are not limited to topically, respiratorialy, intravenously, orally, intraperitonealy, subcutaneously, intramuscularly, rectally, topically and by implant. With respect to intravenous routes, particularly suitable routes are via injection into blood vessels which supply the target tissue to be treated. The crystallin protein can also be delivered into cavities such for example the pleural or peritoneal cavity, or be injected directly into the tissues to be treated. For oral administration, the crystallin protein can be encapsulated or otherwise provided in an enteric for passage through the stomach and release in the small intestine. Any suitable such enteric formulation or coating can be utilized.

Moreover, a crystallin protein can also be coated onto the surface of a stent or balloon of a catheter such as an angioplasty catheter, or other surgical instrument for application to the interior wall of a blood vessel during angioplasty or other surgical procedure. The crystallin can for instance be applied to the wall of the blood vessel in this manner in the form of a gel or any other appropriate formulation to promote wound healing and/or angiogenesis or epithelial cell migration to the site of treatment.

Suitable pharmaceutically acceptable carriers and formulations useful in compositions embodied by the invention can for instance be found in handbooks and texts well known to the skilled addressee such as Remington's Pharmaceutical Science, 15$^{th}$ ed., Mack Publishing Company, Easton, Pa., United States, the contents of which is incorporated herein in its entirety by reference.

The invention will be further described herein after with reference to a number of non-limiting Examples.

EXAMPLE 1

Tissue Extracts Promoting Endothelial Cell Migration and Proliferation 1.1 Bovine Tissues Targeted for Proteoglycan Isolation A number of bovine tissues were targeted for proteoglycan isolation. These included hide, articular cartilage, ligament, bone, muscle, nasal septum, kidney basement membrane, eye and aorta.

The initial procedure used to isolate crystallin proteins involved mechanically breaking down the tissue into small pieces, followed by washing with water to remove water soluble proteins, and extraction with 4 M guanidium hydrochloride (HCl) or 6 M urea. The crude proteoglycan extracts were then subjected to proteolysis with elastase I. However, trypsin, chymotrypsin or any other suitable protease that releases peptides of suitable size that demonstrate bioactivity can also be used. The digests were tested for their ability to promote endothelial cell proliferation and migration. Extracts containing proteins or peptides having activity were fractionated using ion exchange, gel filtration and RP-HPLC, and screened using endothelial cell proliferation and migration assays to identify the active constituent(s). Glycopeptides having stimulatory potential were confirmed using an in vivo aortic ring model of angiogenesis provided by Dr Paul Davis of the Wellington School of Medicine, Wellington, New Zealand, based on a modification of the procedure described by Nicosia R. F and Ottinetti A., 1990 and Brown et al., 1996.

1.2 Digestion of Bovine Tissue Proteoglycan Extracts with Elastase I

The proteoglycan extracts identified in Table 1 were prepared for use in this study.

TABLE 1

| Proteoglycan extracts | | |
|---|---|---|
| Sample | Weight (mg) | Sample numbers |
| MLA-Spleen-001F | 10.6 | MLA-008E1 |
| MLA-Eye-001F | 14.6 | MLA-008E2 |
| MLA-Aorta-001F | 11.6 | MLA-008E3 |
| MLA-Hide-001F | 14.8 | MLA-008E4 |
| MLA-Lung-001F | 21.4 | MLA-008E5 |
| MLA-Nasal seputm-001F | 13.3 | MLA-008E6 |
| MLA-Ligament-001F | 18.3 | MLA-008E7 |
| MLA-Collagen-001F | 14.5 | MLA-008E8 |
| MLA-Bone cartilage-001F | 13.3 | MLA-008E9 |

The extracted proteoglycans were weighed and dissolved in 1 mL of 10 mM Tris HCl pH 8.0 containing 20 mM $CaCl_2$. Porcine pancreatic elastase (PPE) Type I E.C 3.4.21.36 (14.3 mg/protein/mL, 6.0 units/mg and 85.8 units/mL where 1 unit is equivalent to 1 μmol of substrate (N-Succinyl-Ala-Ala-Ala-pNA) converted at 25° C. under standard conditions) was used to hydrolyse the proteoglycan extracts. One unit (10 μL) of PPE was added and the proteoglycans extracts were hydrolysed at 37° C. for 48 hours. The solid material was removed by centrifugation in microfuge at 13200 rpm for 1 minute at room temperature. The supernatant was filter sterilized and tested for endothelial cell proliferation and migration.

1.3 Preparation of Sample MLA-Eye-001F

Sample MLA-Eye-001F was prepared by extracting 17.6 g of minced bovine eye with 200 mL of 4 M guanidinium HCl at room temperature for 2 days. The extract was filtered through Whatman #541 filter paper under vacuum. The filtrate was dialysed against $dH_2O$ and freeze dried until use. Prior to use, the freeze dried material was redissolved in 100 mM Tris HCl pH 8.5 buffer containing 10 mM calcium chloride and subjected to digestion with elastase I. The MLA-Eye-001F preparation was coded MLA-008E2 as indicated in Table 1. The other proteoglycans identified in Table 1 were extracted the same way.

1.4 Reverse Phase High Performance Liquid Chromatography (RP-HPLC)

Fractionation of digested proteoglycan extracts was performed by RP-HPLC on a Phenomenex Jupiter 4μ Proteo 90 Å (250×4.06 mm) with a Phenomenex SecurityGuard C-12 guard column (Phenomenex Corporate Headquarters (U.S.A.), Torrance, Calif., United States.). The column was equilibrated with 0.1% TFA in milli-Q water, using a flow rate of 1 mL/min. A gradient of buffer B (70% acetonitrile 30% milli-Q water containing 0.1% TFA) was applied as follows: 0 min 0% B, 5 min 5% B, 10 min 10% B, 25 min 15% B, 30 min 20% B, 35 min 30% B, 40 min 60% B, 50 min 20% B, 55 min 0% B and 60 min 0% B. Absorbance was monitored at 214 nm.

1.5 Isolation and Preparation of Bovine Aorta Endothelial Cells

Bovine aorta where obtained from a local abattoir and clamped at either end. Arterioles were tied off with string. The aorta was washed free of contaminating blood with 2% sucrose solution under sterile conditions. Trypsin was added in PBS buffer and incubated for 30 minutes. The endothelial cell suspension was mixed 1:1 with cell culture media (DMEM containing 20% foetal bovine serum, 2% glutamine and antibiotics). The cells were collected by centrifugation at 960×g for 10 minutes then suspended in media prior to culturing stock cell ampoules. After five cell passages the cells were frozen in 10% DMSO and stored in liquid nitrogen. Cells were revived and grown in the above medium in a 75 $cm^2$ culture flask until 95% confluent. The cells were then harvested for use.

1.6 Endothelial Cell Proliferation

A sterile 96 well plate containing $0.8 \times 10^4$ bovine aorta endothelial cells per well in Dulbecco's Modified Eagle Medium (DMEM) and 10% foetal bovine serum (FBS) was prepared and incubated for 24, 48 or 72 hours. Samples were prepared in triplicate at three different concentrations (neat, $10^{-2}$ and $10^{-4}$). The cells were allowed to adhere for 2 hours at 37° C., 5% $CO_2$ before test extracts were added. After the desired time period the plate was frozen, the cells lysed and cell numbers read using Molecular Probes CyQuant cell proliferation kit (Invitrogen—Molecular Probes, Eugene, Oreg., United States) as per the manufacturers instructions.

1.7 Endothelial Cell Migration

BD Bioscience angiogenesis cell migration assay 24 well plates (BD Bioscience, Franklin Lakes, N.J., United States) were used as per the manufacturers instructions. The migration plate was kept at −18° C. until required. Briefly, bovine aorta endothelial cells were prepared in DMEM and HEPES pH 7.2 at $2 \times 10^5$ cells/mL. A 250 μL volume of the cell suspension ($5 \times 10^4$ cells) were added to the top chamber. Immediately, 750 μL was added to each of the bottom wells using the sample port to the bottom wells. Samples were prepared by adding the glycoprotein extract to 1 mL of DMEM containing HEPES. The plate was incubated for 22±1 hour at 37° C., 5% $CO_2$ atmosphere. Following incubation the media from the upper chamber was carefully removed. The insert was transferred into a second Falcon™ non-TC treated 24-well plate containing 0.5 mL/well of 4 μg/mL Calcein AM in Hanks balanced salt solution (HBSS) and incubated for 90 minutes at 37° C., 5% $CO_2$. Fluorescence of invaded cells was read in a Thermolabsystems Fluoroskan Ascent fluorescent plate reader using bottom reading with excitation/emission wavelengths 485/538 nm without further manipulation.

The cells were labelled post migration with Calcein AM. Stock solution of Calcein AM was prepared by dissolving 1 mg/mL in DMSO. Stock solution 50 μL was added to 12.5 mL of HBSS.

1.8 Rat Aortic Ring Angiogenesis Assay

Rat aorta were removed and cleaned of adhering fatty and connective tissues before being cut into rings of approximately 3 mm width. Fibrinogen was applied to the bottoms of wells of multi-well culture plates and allowed to gel by thrombin action. An aortic ring was then layered on the top of each gel and a further layer of fibrin placed on this. The fibrinogen was prepared in MCDB131 medium (Sigma, United States) supplemented with antibiotics. The double layer of fibrin was then overlaid with MCDB131 medium containing the test extracts. Control wells contained HBSS. Fumagillin (20 μg/mL) was assayed in triplicate as a negative control.

The gels were incubated at 37° C. in an atmosphere of 3% $CO_2$/97% air. The rings were examined using an inverted microscope and the growth of microvessels from their perimeters is observed. Digital pictures were taken of these every 2 days and the extent of microvessel growth relative to the size of the ring was determined using National Institute of Health (NIH) Image software (National Institutes of Health (NIH), Rockville Pike, Bethesda, Md., United States, and the rate of growth of microvessels was then determined for each well. Each test extract was assayed in triplicate and the mean growth rate was calculated.

2. Results and Discussion

Proteoglycan extracts were prepared and hydrolysed with elastase I. Crude extracts were initially tested for their ability to promote endothelial cell migration or proliferation. The extracts demonstrating activity were fractioned using RP-HPLC. The separated peptides were re-tested to identify the peptide(s) responsible for activity.

The results showed that most of the samples had effectively no stimulatory angiogenic effect. However, measurable stimulation of angiogenesis was observed by extract MLA008E2. VEGF at a concentration of 125 ng/mL was used as the positive control. The Falcon plate used during the assay was tested for background fluorescence. This figure was deducted from the final reading (ie., results-plate blank). The 9 readings taken for each well were averaged, and high and low values plotted. The results are shown in Table 2 and FIG. 1, respectively. An example of the aortic ring assay showing stimulation of angiogenesis by MLA008E2 is shown in FIG. 2.

TABLE 2

Results from in vitro angiogenesis assays performed on tissue extract MLA008E2

| Sample | Rate of microvessel growth | Stimulation/ inhibition |
|---|---|---|
| Control (HBSS) | 12.462 ± 0.87 | — |
| Fumagillin (20 μg/ml) (negative control) | 9.462 ± 1.67 | 24.07% inhibition |
| MLA008 2 # 31-38 (1.0 μg/mL) | 13.197 ± 2.04 | 5.90% stimulation |
| MLA008 2 # 33 (2.57 μM) | 14.1 ± 2.69 | 13.13% stimulation |

The endothelial cell migratory potential of MLA008E2 was also tested. Briefly, proteoglycan extract MLA008E2 was tested in triplicate using two different doses of 10 μL and 50 μL of extract in a total volume of 750 μL of serum-free DMEM under sterile conditions. The results are shown in FIG. 3 which indicate cell migration increased in a dose dependent manner suggesting the presence of endothelial cell migration stimulatory agent(s) in the extract.

Further studies subsequently focused on extract MLA008E2 as a source of peptides/proteins having the ability to modulate angiogenesis.

EXAMPLE 2

Fractionation of MLA008E2 by RP-HPLC or Gel Filtration

The initial fractionation of MLA008E2 involved RP-HPLC separation on an analytical Phenomenex Jupiter 4μ Proteo 90 Å (250×4.06 mm) column with a Phenomenex SecurityGuard C-12 guard column as described in Example 1.4. This column is designed to bind peptides smaller than 10 kDa. Fractions were pooled and tested for endothelial cell migratory potential ($5 \times 10^4$ cells/well in serum free medium were allowed to migrate for 22±1 hour at 37° C. in 5% $CO_2$) and proliferative activity. For the proliferation assay, a cell blank provided the background level of proliferation. 10% FBS provided the positive cell proliferation control. Cell proliferation was tested over a 72-hour period using an initial seed density of $1 \times 10^4$ cells per well in DMEM containing 1% FBS. Cell numbers were quantified using Molecular Probes CyQuant kit as per the manufacturers instructions.

Several fractions were identified as having the potential to promote endothelial cell migration. Specifically, fractions 11-15, 16-20, 21-25, 26-30 and 31-35 (40 fractions in total) appeared to contain agents that stimulated bovine endothelial cells to migrate compared to the background level of migration (cells and media). Single fractions were chosen from within the initial groupings that appeared by thin layer chromatography (TLC) analysis to contain a representative peptide profile (fractions 12, 13, 17, 22, 24, 26, 31 and 33). The individual fractions were re-tested for their endothelial cell migration activity. Fractions 12 and 33 appeared to have the ability to enhance endothelial cell migration, (the higher the emission being indicative of the greater the number of cells that have migrated). Fractions 12 and 33 were further fractionated using gel filtration on a TSK2500 column.

There were multiple peptides present in fraction 12 and one main peak present in fraction 33. The unknown agents in fraction 33 were analysed. Briefly, the compound was analysed by UV/Vis spectrometry and fluorescent spectrometry, proton and $^{13}C$ NMR and IR. The result of the analysis of fraction 33 implied that the major constituent was tryptophan. Tryptophan was tested for its ability to promote endothelial cell migration and surprisingly, appeared to be able to promote migration of the cells. Without being limited by theory, the cell migration associated with endothelial cells is believed to be due to the breakdown of tryptophan induced by both tryptophan dioxygenase and indoleamine 2,3-dioxygenase. Both of these enzymes use superoxide to catalyse the cleavage of the indole ring producing N-formyl kynurenine, and are thereby anti-inflammatory because they scavange oxygen radicals. Thus, tryptophan breakdown leads to both a stimulation in angiogenesis and a reduction in inflammatory damage induced by inflammatory cells present in the wound (e.g., neutrophils).

2.1 Fractionation of MLA008E2 fraction 12 by Gel Filtration.

Fraction 12 was further fractionated on a TSK2500 gel filtration column. The column was equilibrated with phosphate buffered saline and 100 μL of sample was applied to the column at a flow rate of 1 mL/min. The elution profile was monitored at 280 nm and 214 nm. Fractions of 1 mL were collected for a period of 60 minutes. The resulting fractions were retested for their ability to promote endothelial cell migration. The results were inconclusive. It was, therefore, postulated that synergy between these peptides may have caused the initial observation or that higher concentrations of the peptides were needed to produce an effect. MLA008E2 RP-HPLC fractions were retested ($2\times10^5$ cells in serum free DMEM were allowed to migrate for 22±1 hours at 37° C. in 5% $CO_2$) in the absence of 1% FBS.

2.2 Angiogenesis Assays

Additional analysis of several of the MLA008E2 fractions was performed using the rat aortic ring assay (in vitro angiogenesis) as described in Example 1.8 and a rat dorsal flap assay (wound healing assay). The results of these assays are given in Table 3.

TABLE 3

Angiogenesis assay results for fractions of extract MLA008E2

| Sample | Protein Concentration | Mean growth rate | Image | Percentage stimulation or inhibition |
|---|---|---|---|---|
| Control (batch 1) | | 12.5 ± 0.9 | A | |
| Fumagillin (negative) | 20 μg/ml | 9.5 ± 1.7 | B | 24.1% inhibition |
| MLA008E2 # 31-38 | 1 μg/mL | 13.2 ± 2.0 | C | 5.9% stimulation |
| MLA008E2 # 33 | 1 μg/mL | 14.1 ± 2.7 | D | 13.1% stimulation |
| Control (batch 2) | | 12.5 ± 2.2 | E | |
| Fumagillin (negative) | 40 μg/ml | 5.4 ± 1.6 | F | 57.7% inhibition |
| VEGF (positive) | 40 μg/ml | 13.9 ± 0.2 | G | 11.1% stimulation |
| MLA008E2 3-15 | 1 μg/mL | 16.1 ± 0.6 | H | 28.6% stimulation |
| MLA008E2 16-29 | 10 μg/mL | 14.1 ± 1.4 | I | 12.7% stimulation |

The initial batch of samples analysed suggested some stimulation was present in fraction MLA008E2 #33 (corresponding to the fraction containing tryptophan). A further batch of samples analysed indicated that a somewhat similar amount of stimulation was present in extract MLA008E2 3-15. A similar level of stimulation was observed between MLA008E2 #33 of the initial batch and MLA008E2 16-29 of the further batch.

A rat dorsal flap assay provided by a Dr Paul Davis of the Wellington School of Medicine, Wellington, New Zealand, was also employed to assess angiogenesis (see Mellin et al., 1992). Briefly two full skin thickness wounds 8 mm in diameter were made on the dorsal surface between the shoulder blades, along the spine of 6 male Lewis rats aged between 25 and 26 weeks (average 25.3 weeks). The first wound was approximately 6.0 cm distal to the skull and the second a further 2 cm distally along the same line. The animals were anaesthetised with an injection (i.p.) of ketamine (100 mg/kg body weight) and xylazine (5 mg/kg body weight) prior to wounding. After recovery, a sub-cutaneous injection of Temgisic is given at 0.05 mg/kg body weight).

Each animal received 4 doses (25 μL each dose) of the test extract MLA008E2 3-15 which corresponds to MLA-KDJ 007 in phosphate-buffered saline (PBS) (1 μg/mL) applied topically to one of the wounds on days 1, 3, 5, 7 and 9. The peptide solution was filter sterilised. Some material was retained on the filter. To the other wound, 25 μL of PBS only was applied, so each animal had its own control wound. Photographs of each wound were taken prior to each addition using a Canon EOS 3000N camera (F2.8 Macro lens) and Fuji Professional 400NPH film. Prints of each exposure were recorded digitally and the area of each wound calculated from these images using NIH Image 1.63 software. This was continued to Day 17. The mean area of treated wounds and of control wounds were calculated for each time point and mean size of the treated wound to that of the control wound was calculated. The results are shown below in Table 4, and FIGS. 4A and 4B.

TABLE 4

Percentages of original area for treated and control wounds

| Day | Experimental Wound Area | Control Wound Area | Ratio |
|---|---|---|---|
| 1 | 100.00 ± 0.00 | 100.00 ± 3.92 | 1.00 |
| 3 | 82.12 ± 5.70 | 92.10 ± 3.87 | 0.89 |
| 5 | 72.32 ± 3.89 | 84.45 ± 3.69 | 0.86 |
| 7 | 56.72 ± 5.88 | 72.22 ± 3.78 | 0.79 |
| 9 | 26.09 ± 2.07 | 55.23 ± 7.72 | 0.47 |
| 11 | 13.88 ± 1.43 | 39.85 ± 5.47 | 0.35 |
| 13 | 10.93 ± 1.41 | 24.81 ± 1.49 | 0.44 |
| 15 | 4.59 ± 1.30 | 18.34 ± 1.53 | 0.25 |
| 17 | 0.51 ± 0.51 | 10.99 ± 1.03 | 0.05 |

As can be seen, the rate of wound healing was accelerated dramatically between days 7 to 9 for the test wounds compared to the control wounds over the same time period. In addition, complete wound closure was achieved earlier than the control wounds. The faster closure rate suggests that the wound healing process is stimulated at a number points along the wound healing cascade leading to faster wound closure.

2.3 Analysis of Compounds with Stimulatory Properties Derived from MLA008E2

The molecular weights of the peptides/proteins present in the extracts having activity were estimated by gel filtration. A TSK2500 gel filtration column was equilibrated with phosphate buffered saline and 100 μL of sample was applied to the column at a flow rate of 1 mL/min. The elution profile was monitored at 214 nm. Fractions of 1 mL were collected for a period of 60 minutes. Proteins, peptides and amino acids of known relative molecular weight were run under the same conditions to calibrate the column. The results are shown in Table 5.

TABLE 5

Estimation of molecular mass

| Sample | Retention times (min) | Estimated mass (Daltons) ±15% | Stimulation % |
|---|---|---|---|
| MLA008E2 #33 | 5.448, 7.148, 20.527, 25.327 | 45962, 34538, 3644, 1627 | 13.13 |
| MLA008E2 3-15 | 8.61, 13.443, 28.533 | 27012, 11988, 948 | 28.62 |
| MLA008E2 19-29 | 8.6, 39.394 | 27058, 152* | 12.66 |

The figures in bold indicate the postulated protein fragments responsible for observed angiogenic stimulation.

A protein with an approximate molecular mass of 27-kDa in both fractions MLA008E2 3-15 and MLA008E2 19-29 containing stimulatory potential indicated that this protein may be responsible for the observed angiogenesis stimulation. N-terminal sequence analysis was subsequently undertaken to identify this protein.

2.4 N-Terminal Sequence Analysis

In order to obtain a sample of the 27 kDa protein, the extract was subjected to preparative SDS-PAGE and the 27 kDa protein excised for N-terminal sequence analysis. The N-terminus was discovered to be blocked. To overcome N-terminal blocking, a further sample of the 27 kDa protein was prepared and digested with trypsin overnight at 37° C. Resulting peptides were loaded onto a C18 Vyadac column (Vyadac Company (Herperia, Calif., United States) and the peaks collected from a 1 hr gradient of 0-100% B (60% acetonitrile+0.1% TFA). The N-terminus of these peptides was subsequently sequenced.

2.5 Identification of βB2 Crystallin

The major and minor sequences identified are shown below.

| | Residue #: | | | | | | | |
|---|---|---|---|---|---|---|---|---|
| | 1 | 2 | 3 | 4 | 5 | 6 | 7 | 8 |
| Major seq.: | I, V | T, Q | L | Y | E | N | P | N |
| Minor seq: | | | | S | G | T | | |

A search was performed using NCBI protein database tool 'Search for short, nearly exact matches' using the sequence LYENPN (SEQ ID No. 4). This six amino acid code was utilised due to the ambiguity of the first two amino acids (residue 1 and 2). A first search yielded homologies with several β crystallin proteins and dynein proteins. A second search was limited to mammalian species yielding homologies to the mammalian βB3 and βB2 crystallins, as well as to dyenin.

Further analysis of crystallin and dynein proteins demonstrated that the target unknown protein of the extract was βB2 crystallin. As extracted from bovine eye, its N-terminus was acetylated and thereby blocked and the two amino acids preceding the sequence LYENPN (SEQ ID No. 4) were IT. Also a trypsin cleavage site N-terminal to I (lysine K) was present in the sequence allowing for the release of the peptide sequenced (see FIG. 5) (SEQ ID No. 1). Furthermore, Dynein is a very large protein (474610 Da) and sequence preceding the matching sequence was NV. No trypsin cleavage site preceded this sequence. The full sequence ITLYENPN (SEQ ID No. 5) was also used to search the NCBI database which confirmed the identity as βB2 crystallin. The bovine βB2 crystallin amino acid sequence is set out in FIG. 5 (SEQ ID No. 1).

EXAMPLE 3

Purification of βB2 Crystallin from Bovine Eye and Assessment of Wound Healing Activity βB2 crystallin was partially purified using two different approaches that involved gel filtration chromatography on Sephacryl 300HR and ultrafiltration using several nominal molecular weight cut-off membranes. αB crystallin was purified ion exchange chromatography on DEAE Sepharose fast flow.

3.1 Extraction of Bovine Eye Lens Crystallins

Fresh bovine eyes were obtained from an abattoir and processed immediately. To obtain the eye lens, a scalpel was used to slice a 2-3 cm incision between the sclera and the pupil. The lens was forced from the eye by pressing a thumb on the pupil. Using this approach intact lens were recovered with a minimum of unwanted tissue attached. Alternatively, the lens was removed from the eye by making an incision through the centre of the cornea. This incision reached into the lens cutting through the lens sheath, and spanned the diameter of the cornea. This allowed removal of the lens from the eye free of lens sheath and other materials by gently squeezing the eye from either side. Removal of the lens sheath was essential to allow solubilisation of the soluble crystallin proteins within 30 minutes when extracted with distilled water by simple agitation or mixing. Otherwise extraction of the crystallins from the lens required overnight stirring at 4° C. in 10 volumes (w/v) of either distilled water or 100 mM phosphate buffer pH 6.8 containing 1 mM DTT and 150 mM NaCl. The lens slowly dissolved during this period. Insoluble membrane bound proteins were separated from the highly soluble crystallins by ultracentrifugation at 50 000 rpm for 30 minutes. The supernatant containing the water soluble lens crystallins were further fractionated by gel filtration chromatography on a 1 L column containing Sephacryl 300 HR. Gel filtration was performed using several different conditions. The column was run in either distilled water or using extraction buffer 100 mM phosphate buffer pH 6.8 containing 1 mM DTT and 150 mM NaCl. The flow rate was 1 mL/min and 18 mL fractions were collected. Routinely 25 mL of a 45 mg/mL eye lens extract was loaded onto the column. The column was run at 4° C. using a BIORAD Biologic chromatography system using a QuadTec detector set at 214 nm and 280 nm with inline conductivity monitoring to monitor protein elution.

3.2 Purification of Crystallin Proteins

A typical elution profile for bovine crystallin extract is given in FIG. 6. Elution was performed at 1 mL/min and protein was monitored at 214 nm (triangle) and 280 nm. The extract typically contained around 45 mg/mL of protein following ultracentrifugation to remove insoluble material. Peaks resulting from the separation of the various mammalian crystallin proteins were distinguished in the elution profile by relative molecular weight and immunoblot analysis, and by comparing the elution profile to profiles previously described in the literature for crystallin protein. The eluted peaks were identified as representing fractions Alpha, B H, B L1, B L2, Gamma S and Gamma BC/DE, previously shown to separate under gel filtration chromatography by Herbrink and Bloemendal., 1974. The relative protein concentrations of the respective fractions are outlined in Table 6.

TABLE 6

Protein concentration of bovine β crystallin fractions

| Protein fraction | Protein concentration (mg/mL) |
|---|---|
| Alpha | 2.47 |
| Beta H | 1.49 |
| Beta L1 | 1.55 |
| Beta L2 | 1.42 |
| Gamma S | 1.87 |
| Gamma BC/DE | 0.15 |

The six fractions obtained from the gel filtration column containing all the crystallin proteins were analyzed by SDS PAGE analysis.

Crystallin βB2 was present in all β fractions (β H, β L1 and β L2). Recovery of βB2 crystallin from β H fraction was attempted through a pH shift. The pH was reduced from 6.8 down to 5.3 to ionize the histidine residues on the surface of βB2 crystallin which has been suggested to lead to the dissociation of the beta H crystallin aggregate and the formation of a βB2 crystallin dimers of 46-48 kDa that may be separated by gel filtration. The elution profile is shown in FIG. 7. Elution was performed at 1 ml/min and protein was at 214 nm (triangles) and 280 nm.

The βB2 dimer was eluted with a maximum absorbance in fraction 42. The fractions containing this protein were pooled, dialysed and freeze dried. The beta H fraction appeared to contain alpha crystallins which were readily separated using gel filtration at pH 5.3 from the dimer βB2 crystallin. When the pH was adjusted using acetic acid no precipitate formed. This fraction was pooled and verified as containing βB2 crystallin and is referred to below as preparation "Wound Heal 1".

When a crude bovine crystallin extract was fractionated in a similar fashion by adjusting the pH of the extract from 8.6 to 5.0 using glacial acetic acid a white precipitate formed which was removed by centrifugation. The pellet was dissolved at pH 9.0 in 0.1M borate buffer. Western blot analysis suggested that alpha crystallins were present in the protein precipitate that formed at pH 5.0. The presence of βB2 crystallin could not be detected.

3.3 Ultrafiltration for the Purification of Bovine βB2 Crystallin

Based on the above findings, an ultrafiltration separation technique for purification of βB2 crystallin was devised. A range of ultrafiltration membranes were evalutated in order to fractionate bovine crystallins in a method that was more amendable to scale up. The purification of βB2 crystallin was undertaken using a process that utilizes the intra-molecular interaction between βB2 crystallins and the other crystallin proteins.

A bovine crystallin extract containing all of the water soluble crystallins was initially prepared from lens tissue by extraction with distilled water, the extract having a pH of about 6.8, followed by fractionation in distilled water, initially using a 300 kDa nominal molecular weight cut off membrane (NMWCO) in a pressure cell at 70 psi and at 4° C. A gel formed on the membrane which was predominately composed of alpha crystallins and β crystallins. The gel was collected and a portion dissolved in water and analyzed by gel filtration chromatography, and the remaining gel material was stored at 4° C. in a Petri dish. Gamma crystallins appeared to be absent from this gel.

Further fractionation of the 300 kDa filtrate was performed using a 100 kDa NMWCO membrane under the same conditions as outlined above. The retentate appeared to contain significant levels of βB2 crystallin (23166 Da) and βA3 crystallin (25131 Da), which was further purified by gel filtration on a Sephacryl 300HR column. Gel filtration was achieved by loading 25 mL of extract onto the column equilibrated with distilled water at neutral pH. The flow rate was 1 mL/min and 18 mL fractions were collected which were monitored for protein content at 214 nm and 280 nm using a BIORAD QuadTec Detector. The β crystallin fractions were diafiltered and then freeze dried to produce the second sample tested for wound healing analysis referred to as preparation "Wound Heal 2". The majority of the protein present was βB2 crystallin. A dimer of βB2 crystallin with a small amount of a dimer between βB2 crystallin and βA3 crystallin was observed to elute with a peak at fraction 42, which was equivalent to the β L2 fraction of the bovine crystallin extract eluted using this column.

Further fractionation of the 100 kDa filtrate was achieved using a 50 kDa NMWCO membrane. It was apparent that using a 50 kDa NMWCO membrane allowed separation of monomer gamma crystallins from dimer and trimeric β crystallins. Further concentration of gamma crystallins using a 30 kDa NMWCO membrane was achieved and collection of low molecular weight peptides using a 5 kDa NMWCO membrane was also performed. The fractionation of the bovine crystallin extract is outlined in Scheme 1 below. High molecular weight alpha crystallins were essentially separated from the beta crystallins using a 300 kDa NMWCO membrane. Beta crystallins were fractionated using 100 kDa and 50 kDa NMWCO membranes, whereas the gamma crystallins were separated and concentrated using a 30 kDa and 5 kDa NMWCO membrane respectively. All fractionation steps were performed using a pressure cell at 70 psi and at 4° C. as described above. SDS PAGE analysis was performed to observe the protein profiles present in these various fractions.

The 300 kDa retentate contained predominately alpha A and B crystallins and beta crystallins. High molecular weight non-crystallin proteins that were concentrated using this membrane were also observed the identity of which are unknown. The 300 kDa filtrate, 100 kDa retentate and 50 kDa retentate contained mainly β crystallins. The 50 kDa filtrate, 30 kDa retentate, 30 kDa filtrate and 5 kDa retentate contained gamma crystallin proteins of various sizes.

The gamma crystallins that were present within the fractions have a molecular weight lower than 50 kDa. Alpha crystallin proteins were predominately present in the 300 kDa retentate. The β crystallins were located in the fractions between 300 kDa and 50 kDa.

Scheme 1: Fractionation of bovine crystallins

Bovine crystallin extract ⟶ 300 MW ⟶
300 kDa filtrate ⟶ 100 MW ⟶ 100 kDa filtrate ⟶
50 MW ⟶ 50 kDa filtrate ⟶ 30 MW ⟶
30 kDa filtrate ⟶ 5 kDa ⟶ 5 kDa retentant 3.4 Purification of Bovine Alpha B Crystallin A crude bovine crystallin extract was fractionated using DEAE Sepharose fast flow under denaturing conditions in order to isolate αB crystallin. The column (3×33 cm) (Pharmacia XK-26 column containing GE Healthcare DEAE Sepharose fast flow ion exchange resin.) containing DEAE Sepharose fast flow was equilibrated with 5 mM Tris HCl pH 7.6, 6 M urea, 0.01% DTT. A gradient elution was performed using 50 mM Tris HCl pH 7.6, 6 M urea, 0.01% DTT and elution was completed using 35 mM Tris HCl pH 7.6, 6 M urea, 0.01% DTT, 1M NaCl. Protein absorbance was monitored using a BIORAD QuadTec detector at 214 nm and 280 nm. Six mL fractions were collected. 50 mL of bovine crystallin 5 mg/mL was loaded at a flow rate of 1 mL/min.

Fractions under a symmetrical peak off the column were pooled and dialysed using a 12,000 Da nominal molecular weight cutoff membrane against at least three changes of distilled water over 2 days at 4° C. to remove urea. The sample was freeze dried and analyzed using SDS PAGE analysis (FIG. 8). Fractions 37-47 were shown to contain bovine αB crystallin by Western blot and MS analysis. The purified αB crystallin is referred to below as "Wound Heal 3".

3.5 Analysis of Wound Heal Preparations

SDS PAGE and Western blotting analysis was performed to evaluate the enrichment of βB2 crystallin and αB crystallin in the Wound Heal 1, Wound Heal 2, and Wound Heal 3 preparations. The assay for the presence of alpha A crystallin, alpha B crystallin and βB2 crystallin utilized a primary antibody specific for each of these antigens, respectively. The three preparations appeared to be free of alpha A crystallin. Wound Heal 1 and Wound Heal 2 contained βB2 crystallin, whilst Wound Heal 3 contained alpha B crystallin.

Mass spectrophotometer (MS) analysis of the Wound Heal preparations (1-3) was also undertaken. As discussed above, crystallin proteins can undergo post translational modifications. An extensive list of post translational modifications can be found in a review article by Hoehenwarter et al., 2006. βB2 crystallin (23168 Da) was observed in Wound Heal 1. From the MS result, it appears that another protein was present having a mass around 22664 Da. Two proteins were detected in the MS analysis of the Wound Heal 2 preparation, namely βB2 crystallin (23167 Da) and βA3 crystallin (25061 Da). With the number of post translational modifications that have been identified for bovine βB2 crystallin, the mass range for this protein can differ considerably. A peak at 23095 may have resulted from loss of acetyl alanine while a peak at 23335 may be the fully modified form as indicated in FIG. 9 (SEQ ID No. 1).

The closest match from the MS analysis of the Wound Heal 3 preparation was αB crystallin which was also detected by Western blot analysis.

3.6 Wound Healing Assay

Thirty male Lewis rats were divided into 5 groups of 6 rats as outlined below in Table 7. Rats were age and weight matched. Rats were permitted rodent diet and water ad libitum throughout the study.

TABLE 7

Rat treatment protocols

| Group | Treatment | Age (weeks) | Initial Weight range (g) |
|---|---|---|---|
| A | Control | 21.1 | 384-428 |
| B | Bovine extract βB2 crystallin (Wound Heal 1) 0.01 mg/wound | 20.4-21.1 | 382-442 |
| C | Bovine extract βB2 crystallin (Wound Heal 2) 0.1 mg/wound | 20.3-21.1 | 388-444 |
| D | Bovine extract αB crystallin (Wound Heal 3) 1 mg/wound | 20.3-21.1 | 378-420 |
| E | Positive control - *Aloe vera* | 21.1 | 382-436 |

The animals were weighed two days before the start of the trial and weights grouped from lightest to heaviest. Animals were then randomly assigned to groups based on body weights, using 5×5 Latin squares so that group means were as similar as possible.

Rats were housed singly post-operatively. Food consumption was not measured. A daily dose of about 4 ml of jelly was administered from day 1 to assist in rehydration.

Approximately 30 minutes before wounding, each animal was given a subcutaneous injection of Temgesic at the base of the neck (0.075 mg/kg body weight). Each animal was anaesthetised using 3% halothane in oxygen. Once the pedal reflexes had been abolished, the animals were shaved from the base of the skull to the hind limb area using electric clippers. The skin on each rat was disinfected using 0.5% chlorhexidine in 70% ethanol. For each animal, the distance from the base of the skull to the top of the hip joint was measured and the wound position marked with a black felt tip pen, 6 cm below the base of the skull along the spinal axis.

Using asceptic techniques a full thickness incision was made at this position using a sterile 12 mm biopsy punch. Any bleeding was removed using cotton swabs. Care was taken that the punch was dry and that no debris (eg., skin, hair) entered the wounds. Each wound was made at right angles to the surface of the skin and care taken to ensure that the biopsy punch only cut the skin and did not penetrate into the deeper layers of muscle tissue. After photography of each wound using a Canon Digital EOS 20D camera with a F2.8 Macro lens, an aliquot of the sample was applied to the wounds on the rats in Groups A, B, D and E using a Gilson Microman CP 100 positive displacement pipette. The biopsy punch was wiped inside with a swab soaked in sterile saline to remove any tissue fluids and/or debris. The punch was then immersed in 70% ethanol before use on the next animal.

The general condition of each animal was monitored closely for 5 days after wounding. If necessary the animals were provided with additional Temgesic post-operatively. From days 2-7 the animals were provided with toweling. Changes from toweling to shavings were made only when wounds had dried.

All animals had a total of five topical applications of control or test agents on days 1, 3, 5, 7 and 9. For applications and photographs after day 1 the animals were restrained without being anaesthetised.

At the termination of the study, when the wounds were healed, the animals were euthanised by $CO_2$ inhalation and cervical dislocation. The entire wound site including adjacent skin, fascia and muscle tissue was excised and fixed in formalin for histological and immunohistochemical examination. After less than 24 hours in formalin, the wounds were embedded in paraffin wax and three µm thick sections cut, attached to poly-L-lysine coated glass slides, and dewaxed and stained with haematoxylin, eosin and van Gieson stain for histological examination. Other sections were used for immunohistochemistry.

Body weights were measured on days 1, 3, 5, 7, 9, 11, 13, 15, 17, 19, 21 and 23 and deviations from original body weights (on day 1) calculated for each animal. On the same days, photographs were taken using a Canon Digital Eos 20D with a F2.8 Macro lens. Photographs were downloaded and wound areas measured using NIH Image J 1.633u software (National Institutes of Health (NIH), Rockville Pike, Bethesda, Md., United States). A laser speckle image was also taken at the same time as each space photograph was taken. Animals were weighed every second day when the photographic record of wound closure rate was also made.

The redness and swelling of each wound were individually scored from visual observation. These were scored on a scale of 0-3 as follows:

| 0 = No redness or swelling | 1 = Slight redness/swelling |
|---|---|
| 2 = Significant redness/swelling | 3 = Extensive redness/swelling |

Descriptive statistics were evaluated. Preliminary t-tests examined whether outliers significantly affected results. Major analyses were performed on all data points collected. Preliminary analyses were undertaken on control wounds only using t-tests. Univariate ANOVAs were used to assess differences between treatment and controls and samples nested within treatments. A separate ANOVA assessed whether there was a dose response using the treatment samples only. Assumptions for normality were tested using q-q plots on studentized residuals and heterogeneity of variances were tested using Levene's tests. SPSS 11 for Mac OSX was used for assumption testing and statistical analysis.

As a consequence of the wounding, there was an immediate loss of body weight by the rats (FIG. 10). This was most apparent on day 3. Thereafter, all rats showed a steady increase. The rats whose wounds were treated with the PBS carrier showed the greatest drop. They had lost 7.0% of their starting weight at day 3. However, they steadily recovered and gained weight at a faster rate than any of the other four groups. By day 11 the mean weight for these rats had returned to the starting weights and by the conclusion of the study they were approximately 5.0% heavier than at the start of the study. All four groups that were treated showed an almost identical weight loss initially (5.4% to 5.7%). They then regained their weight. Those receiving the lower doses of the test extract (Group B, 0.01 mg per application; Group C, 0.1 mg per application) showed an almost identical rate of increase. Group B had returned to their pre-wounding weight by day 14 and Group C reached this by day 15. Thus their rates of return were slower than for the untreated controls. The rats that had the highest dose applied (Group D, 1.0 mg per application) appeared to gain weight at a slightly faster rate. They had returned to their starting weight by day 12.

Treating the wounds with aloe vera appeared to have an effect that was similar to αB crystallin extract. The mean weight of these rats was back to the starting weight by day 12 and by the end of the study they were, on average, 4.3% heavier than at the start.

The inflammatory reactions of the wounds as a consequence of the treatments were scored and the outcomes are summarised in FIG. 11.

An inflammatory score was assigned to each wound on each day of the study. It is noted there was an immediate significant inflammatory response by all groups following wounding. The smallest increase was for the Control group that received the carrier only. The groups receiving βB2 crystallin extracts showed a somewhat greater initial response. The response by the group receiving αB crystallin and also the group that had aloe vera applied showed an elevated response also. However after day 3, all groups showed a steady decrease in inflammation for the remainder of the study period. The exception was the carrier control group whose inflammation score reached its highest value on day 5 and decreased thereafter. The results indicate that the crystallin extracts and the aloe vera more rapidly produced an anti-inflammatory response. The aloe vera treated wounds appeared to show the most rapid reduction in the inflammation. In contrast there was little significant effect of the crystallin extracts, regardless of dose level, on the decrease in the inflammatory score. The wound areas of the different treatment groups are shown in Table 8 and FIG. 12.

The rate of wound healing in Group A (Control—PBS treated) was of the order expected. The pattern of healing, with the fastest phase being between days 7 and 11 was also as expected.

The wounds treated with the lowest dose of βB2 crystallin (0.01 mg per dose) (Group B) showed a slightly faster healing rate than the reference group over the first 7 days. After day 7 the healing rate for the group was very similar to that of the Control group. Relevantly, the dose level of the test extract for this group was very low.

The average healing rate for the rats in Group C (received 0.1 mg per dose of βB2 crystallin) was higher than that of the Control group (Group A) over the first 9 days. Thereafter the rate for the two groups was almost identical. It is noticeable that the closure rate over the first 11 days was slightly faster for this group than for the group receiving the lower dose (Group B) indicating a potential dose response.

However, when the Group D (αB crystallin) was applied the rate of healing decreased substantially, with the rate of healing for this group being lower than for the group receiving the carrier only. That is, the 1 mg per kg dose inhibited the rate of healing. On day 3 the wounds were 8.8% larger than were the wounds on the rats receiving buffered saline only. On day 7 they were 7.7% larger and on day 11 they were 28.7% larger. It was only in the final days when the wounds were largely healed that Group D had a similar healing rate to the control group. This result suggests that high concentrations of αB crystallin may be antagonistic to healing.

The wounds treated with the aloe vera gel (Group E) showed an almost identical healing rate to those treated with saline (Group A). This applied for the entire experimental period. Thus, the effect of the positive control was not obvious. There is no apparent reason for this lack of effect of the aloe vera gel.

At the completion of wound healing on day 23 there was no apparent promotion of wound closure from any of the samples tested including the positive control aloe vera gel tested at 20 mg per wound. The reason for this may relate to dosage used which could have fallen outside the therapeutic range. However, there was a statistically significant effect at day 5 of the study where the wound area was significantly smaller for Wound Heal 1 (Group B: βB2 crystallin low dose p=0.045) and Wound Heal 2 (Group C: βB2 crystallin high dose p=0.008). This suggests that promotion of wound healing was observed during the early stages of the healing cascade. There was also a statistically significant difference

TABLE 8

Wound areas of different treatment groups

| Day | PBS | S.E.M | 0.01 mg/wound Wound heal 1 βB2 crystallin | S.E.M | 0.1 mg/wound Wound heal 2 βB2 crystallin | S.E.M | 1.0 mg/wound Wound heal 3 αB crystallin | S.E.M | Aloe vera 20 mg/wound | S.E.M |
|---|---|---|---|---|---|---|---|---|---|---|
| 1 | 100 | 0 | 100 | 0 | 100 | 0 | 100 | 0 | 100 | 0 |
| 3 | 85 | 3 | 86 | 3 | 82 | 1.7 | 93 | 4 | 84 | 1.6 |
| 5 | 80 | 2 | 75 | 2 | 69 | 1.3 | 82 | 2 | 76 | 3.6 |
| 7 | 71 | 3 | 69 | 3 | 67 | 0.9 | 76 | 2 | 68 | 1.5 |
| 9 | 52 | 4 | 54 | 3.7 | 50 | 3.2 | 58 | 4.7 | 48 | 4.4 |
| 11 | 27 | 1 | 32 | 5.4 | 28 | 1.9 | 34 | 1.4 | 29 | 2.3 |
| 13 | 18 | 0.8 | 18 | 1.9 | 20 | 2.4 | 23 | 2.8 | 20 | 1.8 |
| 15 | 13 | 0.7 | 13 | 1.9 | 15 | 2.4 | 15 | 2.6 | 14 | 1.4 |
| 17 | 9 | 0.9 | 8 | 1.9 | 11 | 2.2 | 9 | 1.9 | 8 | 0.6 |
| 19 | 5 | 0.9 | 4 | 1.6 | 6 | 2.2 | 5 | 1.3 | 3.8 | 0.7 |
| 21 | 3 | 1 | 1.7 | 0.7 | 4 | 1 | 2.5 | 0.6 | 1.8 | 0.4 |
| 23 | 1 | 0.4 | 1.4 | 0.7 | 1.8 | 0.8 | 1.4 | 0.5 | 0.73 | 0.2 | between βB2 crystallin (Group C) and αB crystallin (Group D) at day 5 (p=0.012). A concentration effect appeared to be evident at day 5 as the lower concentration of βB2 crystallin (Group B) mean wound area was 122.7±14.7 mm whereas that for the higher concentration (Group C) mean wound area was 112.7±10 mm. Therefore, some wound healing activity was apparent from the administration of intact βB2 crystallin.

Analysis of the phosphorylation state of βB2 crystallin was undertaken using $^{31}$P NMR. No peaks were detected suggesting that the protein was not phosphorylated. This was confirmed using a fluorescent phosphoprotein stain (data not shown), further suggesting that βB2 crystallin has bioactivity in wound healing during the early stages of the wound healing cascade around day 5 that is most likely due to its ability to promote angiogenesis.

A low concentration of Wound Heal 1 was used in this assay since at higher protein concentrations, βB2 crystallin forms dimers and higher order aggregates. Wound Heal 2 contained a higher concentration of βB2 crystallin and so may form dimers with another protein that was also present in this extract, βA3 crystallin. The activity of the βB2 crystallin was lower than expected with only a slight decrease in wound area at day 5 compared to the other treatments. The observed lack of dramatic wound healing effect that was initially observed for βB2 containing preparations appears to be due to the lack of treatment of the βB2 crystallin with elastase I to cleave the C-terminal and N-terminal ends of the protein thereby generating the monomeric form of the protein.

EXAMPLE 4

Analysis of Bovine Crystallin Fractions Prepared

Studies were undertaken to investigate the functional properties of crystallin proteins. Fractionation of bovine crystallin proteins using gel filtration chromatography on Sephacryl 300HR was undertaken as described in Example 3. The fractions identified as alpha crystallins as well as beta H, beta L and beta L2, gamma S and gamma BC/DE were separated using this technique. The fractions were then used in the following studies to evaluate biological activity.

4.1 Protease Inhibitory Activity of Crystallins

The bovine crystallin fractions were tested for ability to inhibit elastase I activity. Briefly, a small amount of elastase inhibition was observed with a crude bovine crystallin extract and alpha A/B crystallin fraction. No activity was detected in the β crystallin fractions (beta H, L1 and L2 all containing βB2 crystallin). Gamma S crystallin was shown to have considerable elastase inhibitory activity when compared to the other fractions. These results again demonstrate the differences between α and β crystallins and indicate the protease inhibitory activity of crystallin proteins is restricted to gamma S crystallin and α A and B crystallin which have been shown to also have chaperone activity, as distinct from βB2 crystallin.

4.2 Chaperone Activity

Bovine crystallin fractions were tested for ability to protect the proteases elastase I, trypsin and chymotrypsin from heat denaturation. Briefly, the proteases were heated in a boiling water bath for 30 seconds in the presence or absence of the crystallin fractions. The results are shown in FIG. 13.

The control demonstrated the amount of protease activity before heating and the heat denatured control (HD) demonstrated the amount of protease activity remaining after being heated in the water bath. Chaperone activity was observed when elastase I was mixed with Wound Heal 3 but not with Wound Heal 1 or Wound Heal 2 preparations. Effectively no chaperone activity was observed when the samples were treated with trypsin or chymotrypsin. αB crystallin and αA crystallin isolated by SP Sepharose fast flow were both able to protect elastase I from heat inactivation. Alpha B crystallin appeared to be the most active with respect to protecting elastase I heat denaturation. No activity was observed with any of the β crystallin containing fractions demonstrating the inability of β crystallin to act as a molecular chaperone and protect elastase I from heat mediated denaturation. In contrast to βB3 crystallin, βB2 crystallin was found to be unstable to heat treatment.

4.3 Promotion of Angiogenesis

Four separate studies were carried out to determine the angiogenic effect of crystallin preparations. Each sample was assayed in triplicate. A positive control (VEGF) and a vehicle control containing PBS was also run in triplicate. The percentage standard deviation (from the average) was assessed and outliers removed when variability was found to be greater than 20%. Preliminary statistical significance was assessed with an independent Student t-test at α<0.05. Graphical representation of averages +/− standard errors were determined.

The first study investigated the angiogenic potential of bovine fractions prepared by gel filtration analysis as described in Example 3.2. As described in that Example, the alpha fraction contained αA and αB crystallin, the β H fraction contained all β crystallins, the β L1 fractions contained a sub-fraction of beta crystallins and a high content of βB2 crystallin and beta B3 crystallin and the beta L2 fraction contained only βB2 crystallin and βA3 crystallin.

The second study investigated the angiogenic potential of purified crystallin proteins. Briefly, βB3 crystallin was prepared by heating (97-99° C. for 3 minutes, supernatant collected by centrifugation) and was essentially homogenous. Alpha A crystallin and αB crystallin samples were prepared by ion exchange chromatography as described above and were also essentially homogenous. The Wound Heal 1-3 preparations were also tested in this study.

The third study investigated the angiogenic potential of ovine crystallin proteins compared to their bovine equivalents. Both bovine and ovine crystallin proteins were purified essentially to homogeneity by RP. HPLC using a C4 column, as described below in Example 5. Homogeneity was confirmed by SDS-PAGE. The effect of elastase I treatment of βB2 crystallin was also investigated by comparing the angiogenic potential of intact βB2 crystallin (i.e. undigested) with elastase I digested βB2 crystallin. Elastase I treatment releases the N-terminal and C-terminal extensions of the crystallin protein leaving a globular protein that is monomeric.

In the final study, ovine βB2 crystallin was tested alone or in combination with indoleamine 2,3-dioxygenase (IDO) and ovine alpha B crystallin was tested alone or in combination with tryptophan dioxygenase (TDO)

Briefly, in each study, a single Lewis rat was euthanised and its aorta transferred to a 15 mL Falcon tube containing 10 mL of MCBD-131 medium and stored on ice. After transferring the aorta to a 92×17 mm petri dish containing 10 mL of ice cold MCDB-131, the outer fatty tissue was removed under an Olympus SZ-60 Dissecting microscope. This was undertaken with fibre optic lamp illumination. The aorta was then cut into sequential rings approximately 2 mm in size. Connective tissue was removed with micro scissors and forceps from the outside of the individual rings. Clean rings were stored in a separate petri dish in sterile MCDB-131 medium. Rings were pre-incubated overnight at 37° C. in an atmosphere of 97% air/3% $CO_2$.

To prepare gel sandwiches, 75 mg of fibrinogen was added to 25 mL MCDB-131 medium and shaken gently on a rocker roller for 5 minutes. 3 ml of MCDB-131/fibrinogen solution was added to a 15 mL Falcon tube, followed by 10 μL of thrombin and quickly mixed. A 0.4 mL volume of this fibrinogen-thrombin solution was added to each well on a 24 well plate, 6 wells at a time. Aortic rings were then placed on the setting gel, pushed gently into the gel and left for 45 minutes. These steps were then repeated so each ring was covered with 0.4 mL of gel. Gels were left to set at room temperature. Samples to be tested were diluted to 100 μg/mL in 5 mL of MCDB-131, and 1.5 mL of each sample placed in each of three appropriate wells. The plate was then placed in incubator (37° C., 97% air/3% $CO_2$).

Culture plate were examined daily for signs of infection (fungal growth or yellowing of media) in the wells using an inverted microscope. The growth of microvessels from their perimeters was also observed. Digital photographs of each well were taken seven days after plating using a Pixera PVC-100C digital camera mounted on an OLYMPUS CK-12 microscope and stored on a Macintosh Computer. A low power field (i.e. 20×. A 640×480 pixel PICT) was sufficient. PICT can be converted to grey scale for visualization and measurement in NIH Image. The greyscale image can be opened with the NIH Image program with J 1.32 Image software.

In determining the rate of microvessel growth determination, the area occupied by the microvessel growth around each ring and the area of each aortic ring was determined using the shape tool in NIH image software to draw around the ring. This measurement was repeated, the second time drawing around the capillaries. Typically, 4 measurements were taken—internal and external capillary growth and inner and outer aortic ring area. The ratio of the area of microvessel growth to aortic ring area was then calculated for each well and the mean value and the standard deviation (SD) for each sample of the triplicate determined.

Following digital photography of each individual well, each well was excised and fixed in 10% formalin. After less than 24 hours in formalin, each ring was removed and embedded in paraffin. Three μm thick sections were cut, attached to poly-L-lysine coated glass slides, and dewaxed and pre-digested with protease XIV (0.5 mg/mL in Tris-buffered saline) for 10 min at 37° C. Some antibodies require Heat Induced Epitope Retrieval (HIER) of formalin-fixed paraffin embedded tissue and cytological preparations to 'retrieve' immunoreactivity that has been compromised by processing. Enhanced immuno-staining results were obtained when citrate buffer, pH 6.0 was used. During HIER, tissue slides were immersed in citrate buffer solution and boiled (>95° C.) by hot plate or other appropriate heat source.

HIER treatment consisted of the following steps. Fixed, embedded tissue sections were adhered to a glass slides using HistoGrip™ (Zymed® Cat. No. 00-8050) silane or poly-L-lysine. The immobilized sections were deparaffinzed in xylene and rehydrated in graded alcohols followed by rinsing in deionized water and then in PBS. Endogenous peroxidase was blocked with 0.5% hydrogen peroxide in for 10 minutes, following by further rinsing in PBS. The slides were placed in a slide rack and lowered into a IL glass beaker (Pyrex) containing 500 mL of working solution of citrate buffer. The beaker was placed on a hot plate and the solution heated until boiling and allowed to boil for 15 minutes. After heating, the beaker containing slides was removed from the hot plate and allowed to cool for 25 minutes. Slides were then rinsed with PBS and avidin/biotin blocking performed if necessary. A general protein blocking step was also carried out prior to the immunostaining.

Slides prepared as above were then incubated with primary antibody, incubated with secondary antibody, rinsed, incubated with streptavidin-horseradish peroxidase, rinsed and incubated with DAB chromogen, washed and counter-stained with Mayer's haematoxylin, and washed and mounted using the Innogenex IHC Kit following the instructions of the manufacturer (Affinity Bioreagents, Inc, Golden, Colo., USA)

The slides were specifically stained for Vimentin and CD-31, with primary antibody used at a 1:20 dilution and 1 1:10 dilution, respectively. Staining allowed the ratio of endothelial cells to all migrating cells to be calculated.

4.4 Results and Discussion

In the first study investigating the angiogenic effects of bovine crystallin aggregates, none of the samples were found to stimulate angiogenesis. Relevantly, VEGF at 30 μg/ml did not produce any angiogenic stimulation and indeed, it was 15.08% inhibitory although this was not statistically significant. This was somewhat unexpected and so a higher concentration of VEGF was used in the second study. However, it is believed that experimental conditions were satisfactory as the level of microvessel growth in the control wells (9.640±0.263 SEM) was of the order expected.

The six samples of crystallin aggregates tested contained all the different forms of the crystallin proteins e.g. post translational modifications that include phosphorylation and acetylation and protease degradation products. The alpha crystallins were in high molecular weigh clusters (600 to 800 kDa), whereas the beta crystallins were found to be in tetramers, trimers and dimers ranging in size from 200 to 40 kDa. Size was determined by calibration of the Sepharcyl 300 HR column used for fractionation, SDS PAGE analysis and from the known size ranges reported in the literature.). The gamma crystallins were monomeric with a size range between 20 to 30 kDa.

The second study which focused on the effects of the bovine crystallin proteins and the results are shown in Table 9.

TABLE 9

Angiogenic potential of partially purified bovine crystallin proteins

| Sample | % of Control | % SD | t-test |
|---|---|---|---|
| Control | 100 | 18.8 | |
| VEGF (50 μg/mL) | 107.08 | 7.9 | 0.5845 |
| Bovine αA crystallin (200 μg/mL) | 108.26 | 7.2 | 0.5215 |
| Bovine αB crystallin (200 μg/mL) | 85.21 | 8.2 | 0.2716 |
| Bovine βB2 crystallin Wound Heal 1 (200 μg/mL) | 94.52 | 6.1 | 0.6557 |
| Bovine αB crystallin Wound Heal 3 (200 μg/mL) | 93.09 | 7.1 | 0.5813 |
| Bovine βB2 crystallin Wound Heal 2 (200 μg/mL) | 121.83 | 9.6 | 0.1634 |

As can be seen, βB2 crystallin stimulated a 21.83% increase in microvessel growth at a concentration of 200 μg/mL. A 200 μg/mL solution of αA crystallin was also found to be 8.26% stimulatory. None of the other test samples exhibited an angiogenic effect on microvessel growth. The VEGF at 50 μg/mL produced a slight stimulation although this was not statistically significant. The growth in the control wells (9.894±1.076 SEM) again indicated that the experimental conditions were satisfactory.

The third study compared the angiogenic activity of the ovine crystallin proteins with that of the corresponding bovine crystallin proteins and the results are shown in Table 10.

TABLE 10

Angiogenic activity of ovine and bovine crystallin proteins

| Sample | % of Control | % SD | t-test |
|---|---|---|---|
| Control | 100 | 12.9 | 1 |
| VEGF (50 µg/mL) | 113.7 | 2.7 | 0.15 |
| Ovine βB2 crystallin (100 µg/mL) | 103.5 | 9.8 | 0.73 |
| Ovine βB2 crystallin elastase I digest (100 µg/mL) | 120.8 | 14.1 | 0.17 |
| Bovine βB2 crystallin (non-elastase treated) (100 µg/mL) | 93.4 | 8.3 | 0.50 |
| Ovine αA crystallin (100 µg/mL) | 130.2 | 1.3 | 0.02 |
| Ovine αB crystallin (100 µg/mL) | 97.1 | 12.8 | 0.8 |

Both bovine and ovine αA crystallin were shown to be angiogenic. Ovine αA crystallin was more active than the bovine αA crystallin. However, the latter was tested at half the concentration of the ovine αA crystallin. Therefore, the difference in activity may have been due to a dosage effect. Interestingly, intact bovine and ovine βB2 crystallin were not angiogenic whereas elastase I treated ovine βB2 crystallin stimulated angiogenesis. This result indicates that the monomeric truncated form (i.e. lacking the N-terminal and C-terminal portions) of the protein is more active form in terms of stimulating angiogenesis. Ovine αB crystallin was not found to be angiogenic in this study.

The forth study focused on the effects of crystallin proteins in combination with tryptophan hydrolyzing enzymes IDO and TDO, and the results are shown in Table 11.

TABLE 11

Angiogenic activity of bovine crystallin aggregates

| Sample | % of Control | % SD | t-test |
|---|---|---|---|
| Control | 100 | 12.9 | 1 |
| VEGF (50 µg/mL) | 113.7 | 2.7 | 0.15 |
| Indoleamine 2,3-dioxygenase IDO (100 µg/mL) | 116.4 | 11.3 | 0.31 |
| Tryptophan dioxygenase TDO (100 µg/mL) | 106.2 | 16.6 | 0.76 |
| IDO + Ovine βB2 crystallin (100 µg/mL) | 104.9 | 9.0 | 0.7 |
| TDO + Ovine αB crystallin (100 µg/mL) | 103.82 | 20.3 | 0.85 |

Both IDO and TDO were stimulatory with IDO being more active than TDO. Results for these studies are shown graphically in FIG. 14 and FIG. 15.

In summary, a greater number of activities were evident utilising the purified crystallins suggesting that their biological effects may be somewhat reduced when they are bound in the high molecular weight aggregates. Two samples demonstrated the ability to promote angiogenesis, bovine αA crystallin with 108% activity and Wound Heal 2, bovine βB2 crystallin with 121% activity. VEGF at 50 ng/mL had 107% activity. This was not statistically significant indicating that βB2 crystallin protein is more active than VEGF in promoting angiogenesis in this model system.

These studies demonstrated that crystallin aggregates have low biological activity in the rat aortic ring angiogenesis assay. However, upon further purification of the aggregates, both βB2 crystallin and the elastase I cleavage product of ovine βB2 crystallin and bovine and ovine αA crystallin were demonstrated to have a positive effect on microvessel outgrowth.

EXAMPLE 5

Preparation of Ovine βB2 Crystallin

Purification of ovine βB2 crystallin was performed using a simple efficient process to purify the desired protein. The improved method eliminated the need to perform gel filtration chromatography.

Ovine eyes were collected and the lens removed as described in Example 3.1 above. The lenses were extracted using distilled water. After mixing at 4° C. for 30 minutes the outer layer of the lens had dissolved. The lens extract was centrifuged and the pH adjusted to 4.5 with glacial acetic acid. No precipitate formed during the pH adjustment. The extract was filtered through a 0.45 micron filter prior to loading onto a preparative C4 HPLC column. A single peak containing ovine βB2 crystallin was recovered. Modification of the protocol was used to successfully shorten the elution time required to isolate ovine βB2 crystallin. From two preparative runs 100 mg of purified ovine βB2 was isolated. The yield of βB2 crystallin from ovine lens was 8% of the protein loaded onto the preparative HPLC column. This equates to 2.7% of the lenses' wet weight. The ovine lens contained 34% protein.

5.1 Extraction of Ovine Eye Lens Crystallins

Ovine eyes were obtained from a local abattoir and processed immediately (within 1 hour). A scalpel was used to slice a 1-2 cm incision at various positions on the eye. The 6 lenses recovered were washed with 200 mL of distilled water and the remaining lens sheaths were removed. The water was replaced by 200 mL of fresh distilled water and stirred at 4° C. in 20 volume for 30 minutes. The hard lens nucleus remained intact after this period of time and was discarded from processing. The outer layers of the lens dissolved and a cloudy white solution was obtained which was centrifuged at 30 000 rpm for 30 minutes at 10° C. or clarified using 5000 rpm for 30 minutes at 10° C. The supernatant containing the water soluble lens crystallins was further fractionated using RP-HPLC to determine the potential yield of βB2 crystallin from ovine eyes.

5.2 Preparative RP-HPLC

A preparative RP-HPLC protocol was adapted from the analytical method. Briefly, ovine βB2 crystallins were isolated by RP-HPLC using a Phenomenex Jupiter C4 300A 10 um 250×21.2, Cat. No. 00G-4168-P0, and the SecurityGuard cartridge C4-300A 15×21.2 Jupiter (Serial No. 38833-1). The column was equilibrated with 0.1% TFA in $dH_2O$ and 10% acetonitrile containing 0.1% TFA, flow rate 25 mL/min. A gradient of buffer B (100% acetonitrile containing 0.1% TFA) was applied as follows: 0 min 10% B, 10 min 30% B, 70 min 40% B, 90 min 60% B, 95 min 98% B and 100 min 10%. Absorbance was monitored at 280, 214, 235, 330 and 450 nm. 18 mL fractions were collected every 43 seconds. The load volume was 50 mL (9.57 mg/mL).

A shorter processing time was obtained under the following modified gradient conditions. 0 min 10% B, 10 min 30% B, 15 min 31% B, 20 min 40%, 25 min 60% B, 30 min 98% B and 32 min 10%. Absorbance was monitored at 280, 214, 235, 330 and 450 nm. Again the flow rate was 25 mL/min and 18 mL fractions were collected. Load volume 80 mL (9.57 mg/mL).

5.3 Isolation of Bovine βB2 Crystallin

The peak containing ovine βB2 crystallin was easily separated from the other water soluble crystallin proteins via the RP-HPLC preparative protocol using the Phenomenex Jupiter C4 300A column. A shortened protocol as described in Example 5.2 was used to purify the ovine βB2 crystallin.

The peak containing ovine βB2 crystallin was again separated. A single band was observed by SDS PAGE analysis and under non-reducing conditions the presence of an ovine βB2 dimer was observed. MS/MS analysis of ovine βB2 crystallin revealed a single protein having sequence homology to that of the equivalent bovine βB2 crystallin protein. Fractions 18 and 19 from both runs containing ovine βB2 crystallin were pooled and concentrated under vacuum to remove acetonitrile and then freeze dried to produce a white fluffy protein powder. 100 mg of protein was obtained. The HPLC run was completed within 32 minutes.

5.4 Yield of Ovine βB2 Crystallin

A total of six ovine lenses were collected (4.69 g). This was extracted with 200 mL of water, then 152 mL of this extract was centrifuged (45 mL was not processed 22.5%). After centrifugation, 130 mL was loaded on to the preparative HPLC column as described in Example 5.2 to obtain 100 mg of purified protein. The weight of the various ovine eye tissues and βB2 yield were determined as shown in Table 12 and Table 13.

TABLE 12

Weight of ovine eye tissue

| Tissue | Total Weight (g) |
| --- | --- |
| Ovine eye | 94.65 |
| Ovine lens | 4.69 |
| Ovine vitreous | 66.17 |
| Waste | 23.79 |

TABLE 13

Determination of ovine βB2 crystallin yield

| Protein extract | Volume (mL) | Protein (mg/mL) | Total protein (mg) | Yield (%) |
| --- | --- | --- | --- | --- |
| Water extract | 204 | 9.57 | 1952 | N.D. |
| Load onto HPLC | 130 | 9.57 | 1244 | N.D. |
| Fractions 18 + 19 | 72 | 1.4 | 100 | N.D. |
| Freeze dried protein | — | — | 100 | 8 |

N.D: Not determined

The yield off the column demonstrates that ovine βB2 crystallin comprises around 8% of the protein loaded onto the column. If all the extract was processed it can be expected that another 22 mg of ovine βB2 crystallin would have been obtained.

5.5 Comparison of Sequence Homology of Ovine βB2 Crystallin to Bovine βB2 Crystallin A number of peptides were identified and sequenced for ovine βB2 crystallin that corresponded to the amino acid sequence for bovine βB2 crystallin. The purified ovine βB2 crystallin was subjected to trypsin hydrolysis and MS/MS analysis of the fragments generated. Sequences obtained using LTQ-FTMS were used to search protein databases. The only positive result obtained was for the equivalent bovine protein, βB2 crystallin. The regions of homology were identified using Profound and sequence alignment tools. There were six regions where overlay in sequence was not obtained. The coverage was 51.9%. However, these results confirm with certainty that the ovine protein isolated is ovine βB2 crystallin which has considerable sequence similarity to the bovine protein

EXAMPLE 6

Ovine βB2 Crystallin Wound Healing Preparations 6.1 Preparation of Ovine βB2 Crystallin Ovine eyes were collected essentially as described in Example 5.1 and processed immediately. Briefly, a scalpel was used to slice a 2-3 cm incision across the cornea. The lens was squeezed out of the eye by pinching either side of the eye whilst the blade was removed, allowing about 12 eyes per minute to be processed. The lenses were stirred over night at 4° C. in 20 volumes (w/v) of distilled water. The lens slowly dissolved during this period. A cloudy white solution was obtained, which was filtered through Celite (Celite 545 34967-0025, Acros Fine Chemicals, Belgium,). The pH of the supernatant containing the water soluble lens crystallins was adjusted to 3.5 using acetic acid and βB2 crystallin was purified using RP-HPLC as described in Example 5.2.

6.2 βB2 Crystallin Protein Acidic Precipitate Gel

Protein gel precipitates of ovine βB2-crystallin were prepared making use of the proteins capacity to spontaneously precipitate in the presence of salt solutions under acidic conditions.

A transparent βB2-crystallin acidic gel was prepared as follows. Intact ovine βB2 crystallin purified by preparative RP-HPLC as described in Example 6.1 was dissolved at 85 mg/mL to 100 mg/mL in distilled $H_2O$. The formation of a transparent acidic gel with a pH of about 1.4-1.7 was evident after the protein had completely dissolved. When an elastase I truncated form of the RP-HPLC purified ovine βB2 crystallin was dissolved at its maximum solubility (20 mg/mL) it was unable to spontaneously form a transparent gel. Briefly, the elastase I truncated form of the ovine βB2 crystallin was prepared by RP-HPLC as described in Example 6.1. The truncated form was prepared by digesting purified βB2 crystallin using 1:100 enzyme to substrate ratio of Elastase I (Worthington Biochemical Corporation, Cat. No. 2280 (5.05 u/mg and 27.2 mg/mL) Batch No. 38A10174). Partial hydrolysis of βB2 crystallin was achieved by mixing purified βB2 crystallin 10-50 mg/mL with elastase 0.1-0.5 mg/mL in 10 mM Tris HCl pH 8.0 containing 10 mM $CaCl_2$ for 1 to 8 hours. Upon completion of the reaction the truncated form βB2 crystallin was subjected to RP-HPLC purification. The retention time of the intact form had shifted from around 15 minutes to 10 minutes for the truncated form indicating protein modification. SDS page analysis also demonstrated a shift in the relative molecular weight of the protein. The protein peak that eluted at 10 minutes was collected and solvent removed under vacuum. The protein solution was then freeze dried. The freeze dried truncated protein was mixed with an organogel at 5 mg/g of gel and applied to the wound of a rat at 300 µL per wound per day. Alternatively the freeze dried protein was dissolved in distilled water at 10-20 mg/mL filter sterilized and used to coat gauze presoaked in a salt solution. The protein coated gauze was allowed to air dry. Final sterilization could be achieved using ethylene oxide gas or gamma radiation after packing. This product requires PBS hydration prior to application onto a wound.

6.3 βB2 Crystallin Protein Precipitate Gel Formulated with Calcium Salts

Calcium plays an important role as a modulator in keratinocyte proliferation and differentiation and helps as a regulator in wound healing in the skin. Experimental models have also suggested that management of calcium improves wound management (Lansdown, 2002) and calcium alginate dressings have been shown to improve some cellular aspects of normal wound healing (Doyle et al., 1996). An oily calcium hydroxide suspension when applied topically to oral wounds after non-surgical periodontal therapy has also been shown to improve periodontal wound healing (Kasaj et al., 2006). Further, β-crystallins have been reported to bind divalent calcium ions with defined stoichiometry and moderate affinity (Sharma et al., 1989). In a recent study (Jobby and Sharma, 2007), βB2-crystallin was shown to specifically bind calcium ions.

To provide a βB2 crystallin gel with a higher pH more suitable for application to a wound, intact βB2-crystallin was formulated with calcium salts resulting in a protein precipitate gel with a final pH about 4.0-5.0. Briefly, 0.5 g of purified intact ovine βB2-crystallin prepared as described in Example 6.1 was dissolved in 5 mL of distilled $H_2O$. This resulted in a clear gel like mixture with a pH of around 1.5. This was mixed with 10 mM (final) $Ca(OH)_2$ and 100 mM (final) $CaCl_2$, which resulted in precipitation of proteins. The solution was then centrifuged and the pellet and supernatant separated. The pellet (0.11 g) was dissolved in 3 mL of distilled water and was stored at 4° C. As the supernatant still contained 75% of the initial protein content, it was freeze-dried and a fluffy white powder weighing 0.43 g was obtained. This freeze-dried powder was mixed with the pellet solution, resulting in a gel like product having a pH value at pH 4.0. The final concentration of the gel was 100 mg/mL. This gel was used in a delayed wound healing model described below in Example 8.

6.4 Formulation of a Truncated Form of βB2 Crystallin (Organogel)

A water free organogel (INCI Magnate™, Johnson & Wilkins Limited) containing isopropyl myristate and magnesium stearate was mixed with the RP-HPLC purified ovine elastase I truncated form of βB2 crystallin prepared as described in Example 6.2, at a concentration of 5 mg/mL. The freeze dried protein was mixed evenly into the organogel to form a smooth paste. This paste was used in the 5 day wound healing study described below in Example 7.

EXAMPLE 7

Five Day Wound Healing Study in Rats

A wound healing study was carried out using male 30 Spargue-Dawley rats assigned to 5 treatment groups with 6 rats in each group. The treatment groups were as follows:
Group A—Vehicle control (Organogel)
Group B—Ovine βB2 crystallin treated with elastase I (truncated) (5 mg/g in organogel).
Group C—Ovine αA crystallin (2.6 mg/g in Organogel).
Group D—Bovine indoleamine 2,3-dioxygenase (IDO) (10 mg/g in organogel)
Group E—Positive control (Grapefruit skin extract) (1 mg/g in organogel)

All chromatographic procedures were performed at 4° C. using a BIORAD Biologic system with QuadTec detector set at 214 and 280 nm, with inline conductivity monitoring.

Bovine IDO was prepared from bovine heart tissue as described previously (Shimizu et al., 1978). A cation exchange SP resin (BioRad) was used under the following conditions. The resin was equilibrated using 10 mM $KH_2PO_4$ pH 6.4. Then 10 mL of bovine heart extract (prepared by extracting 25 g of frozen heart with 125 mL of 10 mM $KH_2PO_4$ pH 6.4) was loaded onto the column. The column was washed with 200 mL of equilibration buffer, followed by a gradient elution from 0-1 M NaCl in equilibration buffer over a 200 mL volume. Fractions of 6 mL were collected and tested for IDO activity. Fractions containing activity were pooled, dialysed (10-12 kDa NMWCO) and then freeze dried. The freeze dried protein is referred to as bovine IDO or bovine heart enzyme. The freeze dried protein powder was mixed with an organogel at 10 mg/mL.

Ovine αA crystallin was prepared by using a combination of gel filtration chromatography on Sephacryl 300HR equilibrated and run using 100 mM phosphate buffer pH 6.2 and RP HPLC using the standard protocol outlined in Example 6.1. The load material was the αA and αB fraction off the Sephacryl 300HR column. Purified ovine αA crystallin was confirmed by MS analysis and SDS PAGE analysis.

A positive control (Grapefruit skin extract) was chosen because of its ability to stimulate blood flow as determined by rat aortic ring assay (a model system for vessel formation). A comparison was made between compounds with similar modes of activity as determined by the aortic ring model.

The animal wound model used was essentially as described in Example 3.6. Briefly, approximately 30 minutes before wounding, each animal was given a subcutaneous injection of Temgesic in the fossa region of the groin (0.075 mg/kg body weight). The animals were anaesthetised using 3% halothane in oxygen and once pedal reflexes were abolished, each animal was shaved from the base of the skull to the hind limb area using electric clippers. Skin was disinfected using 0.5% chlorhexidine in 70% ethanol. For each animal, the distance from the base of the skull to the top of the hip joint was measured and the wound position was marked with a black felt tip pen, 6 cm below the base of the skull along the spinal axis. Using asceptic techniques, a full thickness incision was made using a sterile 12 mm biopsy punch, with a gentle rotating motion. The punch was dry and care was taken to ensure that no debris (e.g., skin, hair) entered the wounds. Each wound was made at right angles to the surface of the skin and the biopsy punch only cut the skin and did not penetrate into the deeper layers of muscle tissue. After photography of the wounds using a Canon Digital EOS 20D camera with a F2.8 Macro lens, control or test βB2 crystallin (100 μl aliquots) were applied to wounds using a Gilson Microman CP 100 positive displacement pipette. The biopsy punch was wiped inside with a swab soaked in sterile saline to remove any tissue fluids and/or debris, and the punch was then immersed in 70% ethanol before use on the next animal. The condition of each animal was monitored closely each day after wounding. On each day the animals were provided with new toweling as bedding. All animals had a total of three topical applications of control or test compounds on Days 1, 2 and 3. Photographs were taken of each wound each day.

At the termination of the study, the animals were euthanized by $CO_2$ inhalation and cervical dislocation. The entire wound site including adjacent skin, fascia and muscle tissue was excised, and each was bisected longitudinally. The left piece from animals 1, 2 and 3 of each group was fixed in 4% buffered formalin for 24 hours before being transferred to 70% ethanol. The right pieces from animals 1, 2 and 3 were stored frozen for further protein analyses. Both left and right section from animals 4, 5 and 6 of each group were fixed in 4% buffered formalin. Analysis of the wound area and histological analysis of wounds was undertaken.

The wounds were photographed daily and the images analyzed using NIH image to calculate the wound area. Descriptive statistics were evaluated. Preliminary t-tests examined whether outliers significantly affected results. Major analysis were performed on all data points collected. Preliminary analyses were undertaken on control wounds only using t-tests. Univariate ANOVAs were used to assess differences between treatment and controls and samples nested within treatments. A separate ANOVA assessed whether there was a dose response using the treatment samples only. Assumptions for normality were tested using q-q plots on studentized residuals and heterogeneity of variances were tested using Levene's tests. SPSS 11 for Mac OSX was used for assumption testing and statistical analysis.

The entire wound site including adjacent skin, fascia and muscle tissue was excised and fixed in formalin for histological examination. After less than 24 hours in formalin, the wounds were embedded in paraffin wax and three µm thick sections cut, attached to poly-L-lysine coated glass slides, and dewaxed and stained with haematoxylin and eosin for histology.

Haemotoxylin and eosin stained slides were photographed digitally at low magnification (2.5× objective). Since sections were fairly large, between 6 and 12 photographs were necessary to record each entire tissue section. Sufficient overlap between successive photographs was included to allow overlaying of photographs at a later date to form composite images. Each section was anatomically similar, consisting of two strips of haired skin flanking an ulcerated wound covered by a coagulum of serum, neutrophil debris and scattered bacterial colonies. Deep to this serocellular crust was a layer of fibrovascular granulation tissue that, typically, was stratified into a superficial, highly cellular, compact layer and a deeper, looser layer that variably contained dense capillary networks. In all cases the ulcer penetrated the panniculus muscle layer. Different sections of the wounds were analyzed for inflammatory cells and blood vessel numbers.

The truncated form of βB2 crystallin was found to have the greatest healing response over the 5 day wound healing study compared to the organogel vehicle negative control and the grapefruit positive control. The wound area for the truncated form of ovine βB2 crystallin at day 5 was 69.9±4.4 compared to 83.7±3.4 as indicated in Table 14

αA crystallin (Group C) and indoleamine 2,3 dioxygenase (Group D) had a total capillary count of 9.2 and 8.5 respectively.

Histological analysis undertaken at day 5 revealed the inflammatory cell profile (i.e., macrophages, neutrophils, eosinophils, mast cells and plasma cells) at the wound transition zone was similar for all the test substances. The number of lymphocytes were statically significantly different ($p<0.01$) between all of the test compounds and the vehicle control suggesting that the level of bacterial burden was higher in the test preparations compared to the vehicle only control. This may have resulted in the higher neutrophil content of the test groups compared to the controls.

EXAMPLE 8

Delayed Wound Healing Study 8.1 Ischemic Wound Healing Animal Model

An ischemic delayed healing model based on a model previously described by Chen et al., 1999 was used. The ischemia was caused by placing two incisional wounds (bi-pedicle flaps) either side of the excisional wound in the centre of the animals back. More particularly, male age and weight matched Sprague-Dawley rats were anesthetized with intramuscular ketamine hydrochloride (100 mg/kg body weight). The dorsal hair of each was clipped, and a 10×4 cm clear rectangular template was used to outline the area of study on the back. Under sterile conditions, a full thickness incision was made using a sterile 12 mm biopsy punch, with a gentle rotating motion. Any bleeding was removed using cotton swabs. Care was taken that the punch is dry and that no debris (e.g., skin, hair) enters the wounds. Each wound was made at right angles to the surface of the skin. For the ischaemic group

TABLE 14

Percentage size of wounds with time

| Days after wound admin. | Group A. Organogel vehicle control. Mean % of original wound area (N = 6) | S.E.M | Group B. Ovine meat protein, truncated, 5.0 mg/gm of organogel. Mean % of original wound area (N = 6) | S.E.M | Group C. Ovine meat protein, phosphorylated, 2.6 mg/gm of organogel. Mean % of original wound area (N = 6) | S.E.M | Group D. Bovine heart enzyme, 10.0 mg/gm of organogel. Mean % of original wound area (N = 6) | S.E.M | Group E. Positive control, grapefruit ext., 1 mg/gm of organogel. Mean % of original wound area (N = 6) |
|---|---|---|---|---|---|---|---|---|---|
| 1 | 100.00 | 0.00 | 100.00 | 0.00 | 100.00 | 0.00 | 100.00 | 0.00 | 100.00 |
| 2 | 104.44 | 6.04 | 94.97 | 2.38 | 100.78 | 3.90 | 95.19 | 4.02 | 103.62 |
| 3 | 98.66 | 4.31 | 86.39 | 3.72 | 90.38 | 2.20 | 87.05 | 2.41 | 94.56 |
| 4 | 91.20 | 5.18 | 83.23 | 5.05 | 83.47 | 1.85 | 84.47 | 3.26 | 98.65 |
| 5 | 83.70 | 3.43 | 69.92 | 4.42 | 75.37 | 2.67 | 76.80 | 3.09 | 84.24 |

Analysis of the capillary blood vessel density in the transition zone, the zone between the normal skin and wound, demonstrated a statistically significant increase in vessel density for the elastase I truncated form of βB2 crystallin compared to the vehicle only control as indicated in FIG. 16.

Capillary grading of 1 was observed outside of the wounds for all treatment groups. However, a grading of 6.2 was obtained for superficial cells and 4.0 for deep cells (total 10.2, Group B) for the elastase I truncated βB2 crystallin treatment group compared to 5.5 and 3.3 for the vehicle control (total 8.8, Group A) respectively. The two other treatments using the excisional wound was made as above. In addition, using a scalpel, two longitudinal, full thickness incisions were made on either side of the excisional wound, extending 1 cm above and 1 cm below the top and bottom edges of the wound (~3 cm in length). These wounds were placed ~1.5 cm laterally on either side of the excisional wound. Once haemostasis has been achieved, the wound flap was elevated and the membranes and any blood vessels underlying the wound bed were cut using surgical scissors. The incisions were closed using three interrupted sutures (4-0 Novafil, monofilament polybutester, nonadsorbable suture, Tyco, Cat. No 4402-33) at equidistant points along the length. Once haemostasis has again been achieved the wounds were photographed. After photographing the wounds, the test samples (100 μl of intact ovine βB2 crystallin and 100 μl of Medifill II™ (see Example 8.2)) were applied, using Gilson Microman CP100 & CP1000 positive displacement pipette. The biopsy punch was wiped inside with a swab soaked in sterile saline to remove any tissue fluids and/or debris. The punch was immersed in 70% Ethanol before use on the next animal. Each animal's condition was monitored closely after wounding. On the second and third days after wounding, each animal was given a new towel as bedding. Changes from towelling to shavings was made only when wounds have dried and are not adversely affected by shavings—usually, between Days 5 to 7 of the study. The control group consisted of the excisional wound only. The rate of wound closure was measured over a 31 day period.

The results clearly demonstrated a marked reduction in the rate of wound closure over the full 21 day duration of the experiment, when compared to controls, therefore validating this model of delayed wound healing. A statistical analysis using the student T-test showed that the delay in wound closure was significant at $p:\alpha<0.05$ at all times throughout the trial, from Day 1 onwards.

The delay in wound closure between the ischemic and normal wounds was approximately 4 days for the early portion of the study up until day 13. At this time point the ischemic wounds were approximately twice the size as the wounds in the control animals. By day 15 the percentage of original wound area in the normal wound animals was approximately 10%. The ischemic wounds did not reach this level of closure until day 27 suggesting that the delay had been extended a further 8 days. This result suggested that tissue ischemia causes a significant delay in wound closure. The grooming of wounds was apparent in all treatment groups. Grooming may also increase the likelihood of wound infection which could delay the healing rate.

8.2 Comparative Study

The ischemic delayed wound healing rat model described in Example 8.1 was used to evaluate the wound healing benefit of intact βB2 crystallin compared to a commercially available Medifill II™ Type I bovine collagen (BioCore Medical Technologies, Inc. Silver Spring, Md., United States), wound healing collagen gel containing Type I bovine collagen in the triple helical molecular form specific to wound healing. The enhanced surface area/density of the collagen fibrils increase the level of collagen into contact with the wound surface.

Intact βB2 crystallin protein was chosen over the RP-HPLC purified elastase I truncated form described in Example 6.2, because of the ability of the intact form to form a gel containing intact βB2 crystallin protein in high concentration. Human chronic wounds exhibit high levels of proteases (including human neutrophil elastase), that have the ability to hydrolyze the intact βB2 crystallin leading to the formation of the pro-angiogenic truncated form(s) of the protein.

Briefly, intact ovine βB2 crystallin protein formulated into a protein precipitate gel as described above in Example 6.2 or the Medifill II™ collagen gel (as a positive control) was applied to ischemic wounds in male Sprague-Dawley rats on day 1, 3, 5, 7 and 9. Results were expressed as the mean percentage of the original wound area. The control group consisted of animals with untreated ischemic wounds. All 3 groups contained 10 rats in each (N=10).

The initial five days of the study demonstrated a low level improvement in the healing rate in the βB2 crystallin protein gel treatment group but this was not statistically significant. By day 7 all three treatments had similar wound areas. From day 7 through to the end of the study at day 31 the Medifill™ gel treatment group tracked an essentially identical path as the control ischemic wound indicating it had no real benefit or detriment to the healing rate of the wound. The intact βB2 crystallin gel appeared to slow the closure rate compared to the control ischemic wound between days 9 to 27 but again, this was not significant. At day 27 one of the animals in the intact βB2 crystallin gel had damaged its wound and along with the over grooming, the wound became infected so the wound area became much larger. It was decided to cull this animal on day 27. As a result, the mean results for that treatment group lowered abruptly on day 29. This was a dramatic effect on the wound area average from a single animal. The presence of infection in this animal could cause further delays in healing so removal of this animal from the trial is justified, and this animal was considered to be an outlier. There was no significant difference in the results for the Medifill II™ gel and intact βB2 crystallin gel treatment groups compared to the ischemic control group. The conclusion drawn from this study is that both Medifill II™ gel and intact βB2 crystallin gel provide a similar level of benefit in healing ischemic wounds.

There appeared to be little benefit obtained from the Medifill™ gel compared to the non treated control as the mean percentage of the original wound area was similar throughout the course of the experiment. However, in contrast, the intact βB2 crystallin gel showed some benefit over the ischaemic control wound over the first 5 days of treatment. Over the remaining period of the trial no further benefit was observed compared to the control ischaemic wound until day 31 of the trial. At day 31 the mean percentage of the original wound area for the βB2 crystallin protein was smaller than that for the ischaemic control wounds. Relevantly, the production of the truncated form of βB2 crystallin from the intact protein may have been restricted in the earlier stages of wound healing in this model as the proteases that hydrolyze βB2 crystallin are present in inflammatory stages of wound healing which occur in the first 72 hours. As human non-healing wounds have a prolonged inflammatory phase and exhibit high levels of proteases, administration of the intact form of βB2 crystallin may have greater benefit under those circumstances.

EXAMPLE 9

Preparation of a Gauze for Dressing Wounds

Cloth material gauze or muslin was coated with RP-HPLC purified intact or elastase I treated ovine βB2 crystallin as follows.

The cloth material was placed into a salt solution (10 mM acetic acid pH 3.5 containing 2M ammonium sulfate, although a number of different salts can be used including calcium salts as described above). The cloth was removed from the salt solution and blotted dry on filter paper until essentially free of excess water. No additional water could be removed from the material by blotting between two layers of filter paper. The cloth was then placed into an acidic solution of purified βB2 crystallin (10-50 mg/mL).

βB2 crystallin truncated form was prepared in 10 mM acetic acid pH 3.5. The pH value can range from 2.0 to 5.0. The βB2 crystallin protein concentrations tested were found to effectively coat the cloth. Within about 10 seconds βB2 crystallin coats the surface of the cloth with a white protein precipitate as shown by electron microscopy. The intact form of βB2 crystallin also demonstrated the ability to coat the surface of previously soaked cloth under identical conditions.

The ability to coat bandage or other materials with βB2 crystallin may assist in delivering an effective amount of the protein to a wound site. Both the intact and the elastase I treated truncated forms of βB2 crystallin were found to coat cloth material gauze and muslin. The level of coating may be controlled by altering the salt concentration, protein concentration and the length of time the cloth, gauze or other suitable substrate material is in contact with the βB2 crystallin protein solution. The coated material may then be dried and sterilized (e.g., gamma irradiated) for subsequent use. A sponge material was also coated with ovine βB2 crystallin protein using the above protocol although the sponge was squeezed to remove excess liquid prior to being placed in the βB2 crystallin protein solution. This type of wound dressing may be suitable for use in wounds that produce high levels of exudate.

Although the invention has been described with reference to a number of embodiments it will be appreciated by those skilled in the art that numerous variations and/or modifications can be made. All such variations and/or modifications are expressly encompassed. The present embodiments are, therefore, to be considered in all respects as illustrative and not restrictive.

REFERENCES

Ajaz, M. S., Ma, Z., Smith, D. L., Smith, J. B. (1997). Size of human lens β-crystallin aggregates are distinguished by N-terminal truncation of βB1. *Journal of Biological Chemistry,* 272 (17), pp. 11250-11255.

Bloemendal, H., De Jong, W., Jaenicke, R., Lubsen, N. H., Slingsby, C. and Tardieu, A. (2004). Ageing and vision: structure, stability and function of lens crystallins. *Progress in Biophysics & Molecular Biology* 86: 407-485.

Brown, K J, Maynes, S F, Bezos, A, Maguire, D J, Ford, M D and Parrish, C R (1996). A novel in vitro assay for human angiogenesis. *Lab Invest.* 75: 539-555.

Chen, C., Schultz, G. S., Bloch, M., Edwards, P. D., Tebes, S, and Mast, B. A. (1999). Molecular and mechanistic validation of delayed wound healing rat wounds as a model of human chronic wounds. *Wound Repair & Regeneration* 7: 486-494.

Dirks, R. P. H., Van Genesen, S. T., Kruse, J. J. C. M., Jorissen, L., Lubsen, N. H. (1998). Extralenticular expression of the rodent βB2-crystallin gene [2]. *Experimental Eye Research,* 66 (2), pp. 267-269.

Doyle, J. W., Roth, T. P., Smith, R. M., Li, Y-Q and Dunn, R. M. (1996). Effect of calcium alginate on cellular wound healing processes modelled in vitro. *Journal of Biomedical Materials Research,* 32, 561-568.

Hay, R. E., Petrash, J. M., (1987). Nucleotide sequence of a bovine lens alpha A-crystallin cDNA. Biochem. Biophys. Res. Commun. 148(1), pp 31-37.

Head, M. W., Peter, A., Clayton, R. M. (1991). Evidence for the extralenticular expression of members of the β-crystallin gene family in the chick and a comparison with d-crystallin during differentiation and transdifferentiation. *Differentiation,* 48 (3), pp. 147-156.

Head, M. W., Sedowofia, K., Clayton, R. M. (1995). βB2-Crystallin in the mammalian retina. *Experimental Eye Research,* 61 (4), pp. 423-428.

Hejtmancik, J. F., Wingfield, P. T., Chambers, C., Russell, P., Chen, H.-C., Sergeev, Y. V., Hope, J. N. (1997). Association properties of βB2- and βA3-crystallin: Ability to form dimers. *Protein Engineering,* 10 (11), pp. 1347-1352.

Herbrink and Bloemendal (1974). Studies on β crystallin. Isolation and partial characterization of the principal polypeptide chain. *Biochimica et Biophysica Acta,* 336; 370-382.

Hoehenwarter, W., Klose, J., Jungblut, P. R. (2006). Eye lens proteomics. *Amino Acids,* 30 (4), pp. 369-389.

Jobby, M. K. and Sharma. Y (2007). Calcium-binding to lens βB2 and βA3-crystallins suggests that all β-crystallins are calcium-binding proteins. *The FEBS Journal,* 274, 4135-4147.

Kantorow, M., Horwitz, J. (1997). Extralknicular expression, cAMP-dependent kinase phosphorylation and autophosphorylation of βB2-crystallin. *Investigative Opthalmology and Visual Science,* 38 (4), pp. S205.

Kasaj, A., Willershausen, B., Berakdar, M., Tekyatan, H. and Sculean, A., (2006). Effect of oily calcium hydroxide suspension on early wound healing after non-surgical periodontal therapy. *Clinical Oral Investigations,* 10, 72-76.

Kleiman, N. J., Chiesa, R., Gawinowicz Kolks, M. A., Spector, A. (1988). Phosphorylation of β-crystallin B2 (βBp) in the bovine lens. *Journal of Biological Chemistry,* 263 (29), pp. 14978-14983.

Lansdown, A. B. G., (2002). Calcium: a potential central regulator in wound healing in the skin. *Wound Repair and Regeneration,* 10 (5), 271-285.

Magabo, K. S., Horwitz, J., Piatigorsky, J., Kantorow, M. (2000). Expression of βB2-crystallin mRNA and protein in retina, brain, and testis. *Investigative Opthalmology and Visual Science,* 41 (10), pp. 3056-3060.

McFall-Ngai, M., Horwitz, J., Ding, L.-L., Lacey, L. (1986). Age-dependent changes in the heat-stable crystallin, βBp, of the human lens. *Current Eye Research,* 5 (5), pp. 387-394.

Mellin, T N, Mennie, R J, Cashen, D E et al (1992). Acidic fibroblast growth factor accelerates dermal wound healing. *Growth Factors* 7: 1-14.

Nicosia R F and Ottinetti, A (1990). Growth of microvessels in serum-free matrix culture of rat aorta: A quantitative assay of angiogenesis in vitro. *Lab Invest.* 63: 115-122.

Needleman, S. B., Wunsch, C. D., (1970). A general method applicable to the search for similarities in the amino acid sequence of two proteins". *J Mol Biol* 48(3): 443-53.

Sharma, Y., Rao, M., Narasu, L. M., Rao, C. S., Somasundaram, T., Gapalakrishna, A. and Balasubramanian, D., (1989) Calcium Ion Binding to d- and β-crystallins. *The Journal of Biological Chemistry,* 264 (22), 12794-12799.

Shimizu, T., Nomiyama, S., Hirata, F., Hayaishi, O., (1978). Indoleamine 2,3 dioxygenase. Purfication and some properties. Journal of Biological Chemistry, 253 (13), pp. 4700-4706.

The invention claimed is:

1. A method for treating a wound or promoting angiogenesis in a subject in need thereof, comprising administering an amount of a βB2 crystallin protein or an angiogenic fragment thereof to the subject, effective to treat the wound or promote angiogenesis in the subject, wherein the βB2 crystallin protein or an angiogenic fragment thereof comprises one or more Greek key domains of βB2 crystallin.

2. The method according to claim 1 comprising administering βB2 crystallin protein wherein the protein is a modified form of βB2 crystallin having at least 80% amino acid sequence identity with native βB2 crystallin protein.

3. The method according to claim 1 comprising administering an angiogenic fragment of βB2 crystallin.

4. The method according to claim 3 wherein the angiogenic fragment includes all Greek key domains of βB2 crystallin.

5. The method according to claim 3 wherein the angiogenic fragment is an elastase cleavage product of βB2 crystallin.

6. The method according to claim 3, wherein the angiogenic fragment comprises the C-terminal extension of native βB2 crystallin protein.

7. The method according to claim 6, wherein the crystallin protein is ovine or bovine crystallin protein.

8. The method according to claim 1 wherein the βB2 crystallin protein is an eye lens crystallin protein.

9. The method according to claim 1 wherein the crystallin protein is a bovine or ovine crystallin protein.

10. The method according to claim 1 wherein the crystallin protein or angiogenic fragment is in a topically acceptable composition, and the composition is topically administered to a wound.

11. The method according to claim 1 being a method for treating a wound in skin of the subject.

12. The method according to claim 1 being a method for promoting angiogenesis in the subject.

13. The method according to claim 1, wherein the protein is native βB2 crystallin protein.

14. A method for promoting endothelial cell proliferation and/or migration in a subject in need thereof, comprising administering the subject with an effective amount of a βB2 crystallin protein or an angiogenic fragment thereof, thereby promoting endothelial cell proliferation and/or migration in the subject, wherein the βB2 crystallin protein or an angiogenic fragment thereof comprises one or more Greek key domains of βB2 crystallin.

15. The method according to claim 14 comprising administering an effective amount of native βB2 crystallin to the subject.

16. The method according to claim 14 comprising administering an effective amount of βB2 crystallin protein to the subject, the protein being a modified form of βB2 crystallin having at least 80% amino acid sequence identity with native βB2 crystallin.

17. The method according to claim 14 comprising administering an angiogenic fragment of βB2 crystallin to the subject, the angiogenic fragment comprising the C-terminal extension of native βB2 crystallin.

18. The method according to claim 14 or 17 wherein the crystallin protein is a bovine or ovine crystallin protein.

19. A pharmaceutical composition for treating a wound, or promoting angiogenesis, endothelial cell proliferation and/or migration in a subject, comprising an angiogenic fragment of a βB2 crystallin protein, together with a pharmaceutically acceptable carrier, wherein the angiogenic fragment of the βB2 crystallin protein comprises one or more Greek key domains of βB2 crystallin.

20. The composition according to claim 19 comprising an angiogenic fragment of native βB2 crystallin.

21. The composition according to claim 20 wherein the angiogenic fragment comprises the C-terminal extension of native βB2 crystallin.

22. The composition according to claim 19 or 21 wherein the βB2 crystallin protein is bovine or ovine βB2 crystallin.

23. The composition according to claim 19, wherein the βB2 crystallin protein is a modified form of βB2 crystallin having at least 80% amino acid sequence identity with native βB2 crystallin.

* * * * *

SEQUENCE LISTING

<160> NUMBER OF SEQ ID NOS: 9

<210> SEQ ID NO 1
<211> LENGTH: 204
<212> TYPE: PRT

<213> ORGANISM: bovine

<400> SEQUENCE: 1

Ala Ser Asp His Gln Thr Gln Ala Gly Lys Pro Gln Pro Leu Asn Pro
1               5                   10                  15

Lys Ile Ile Ile Phe Glu Gln Glu Asn Phe Gln Gly His Ser His Glu
            20                  25                  30

Leu Asn Gly Pro Cys Pro Asn Leu Lys Glu Thr Gly Val Glu Lys Ala
        35                  40                  45

Gly Ser Val Leu Val Gln Ala Gly Pro Trp Val Gly Tyr Glu Gln Ala
    50                  55                  60

Asn Cys Lys Gly Glu Gln Phe Val Phe Glu Lys Gly Glu Tyr Pro Arg
65                  70                  75                  80

Trp Asp Ser Trp Thr Ser Ser Arg Arg Thr Asp Ser Leu Ser Ser Leu
                85                  90                  95

Arg Pro Ile Lys Val Asp Ser Gln Glu His Lys Ile Thr Leu Tyr Glu
            100                 105                 110

Asn Pro Asn Phe Thr Gly Lys Lys Met Glu Val Ile Asp Asp Asp Val
        115                 120                 125

Pro Ser Phe His Ala His Gly Tyr Gln Glu Lys Val Ser Ser Val Arg
    130                 135                 140

Val Gln Ser Gly Thr Trp Val Gly Tyr Gln Tyr Pro Gly Tyr Arg Gly
145                 150                 155                 160

Leu Gln Tyr Leu Leu Glu Lys Gly Asp Tyr Lys Asp Ser Gly Asp Phe
                165                 170                 175

Gly Ala Pro Gln Pro Gln Val Gln Ser Val Arg Arg Ile Arg Asp Met
            180                 185                 190

Gln Trp His Gln Arg Gly Ala Phe His Pro Ser Ser
        195                 200

<210> SEQ ID NO 2
<211> LENGTH: 19
<212> TYPE: PRT
<213> ORGANISM: bovine

<400> SEQUENCE: 2

Ala Ser Asp His Gln Thr Gln Ala Gly Lys Pro Gln Pro Leu Asn Pro
1               5                   10                  15

Lys Ile Ile

<210> SEQ ID NO 3
<211> LENGTH: 15
<212> TYPE: PRT
<213> ORGANISM: bovine

<400> SEQUENCE: 3

Arg Asp Met Gln Trp His Gln Arg Gly Ala Phe His Pro Ser Ser
1               5                   10                  15

<210> SEQ ID NO 4
<211> LENGTH: 6
<212> TYPE: PRT
<213> ORGANISM: bovine

<400> SEQUENCE: 4

Leu Tyr Glu Asn Pro Asn
1               5

<210> SEQ ID NO 5

```
-continued

<211> LENGTH: 8
<212> TYPE: PRT
<213> ORGANISM: bovine

<400> SEQUENCE: 5

Ile Thr Leu Tyr Glu Asn Pro Asn
1               5

<210> SEQ ID NO 6
<211> LENGTH: 8
<212> TYPE: PRT
<213> ORGANISM: bovine

<400> SEQUENCE: 6

Ala Ser Asp His Gln Thr Gln Ala
1               5

<210> SEQ ID NO 7
<211> LENGTH: 11
<212> TYPE: PRT
<213> ORGANISM: bovine

<400> SEQUENCE: 7

Gly Lys Pro Gln Pro Leu Asn Pro Lys Ile Ile
1               5                   10

<210> SEQ ID NO 8
<211> LENGTH: 10
<212> TYPE: PRT
<213> ORGANISM: bovine

<400> SEQUENCE: 8

Arg Asp Met Gln Trp His Gln Arg Gly Ala
1               5                   10

<210> SEQ ID NO 9
<211> LENGTH: 5
<212> TYPE: PRT
<213> ORGANISM: bovine

<400> SEQUENCE: 9

Phe His Pro Ser Ser
1               5
```